US009216963B2

(12) United States Patent
Neumann et al.

(10) Patent No.: US 9,216,963 B2
(45) Date of Patent: *Dec. 22, 2015

(54) PYRAZINE DERIVATIVES WITH EXTENDED CONJUGATION AND METHODS OF USING THE SAME IN OPTICAL APPLICATIONS

(75) Inventors: William L. Neumann, St. Louis, MO (US); Raghavan Rajagopalan, Solon, OH (US); Richard B. Dorshow, St. Louis, MO (US)

(73) Assignee: MEDIBEACON INC., St. Louis, MO (US)

( * ) Notice: Subject to any disclaimer, the term of this patent is extended or adjusted under 35 U.S.C. 154(b) by 1076 days.

This patent is subject to a terminal disclaimer.

(21) Appl. No.: 12/305,700

(22) PCT Filed: Jun. 20, 2007

(86) PCT No.: PCT/US2007/014369
§ 371 (c)(1),
(2), (4) Date: Dec. 19, 2008

(87) PCT Pub. No.: WO2007/149478
PCT Pub. Date: Dec. 27, 2007

(65) Prior Publication Data
US 2010/0233091 A1  Sep. 16, 2010

Related U.S. Application Data

(60) Provisional application No. 60/805,568, filed on Jun. 22, 2006.

(51) Int. Cl.
| *A61B 10/00* | (2006.01) |
| *A61B 5/00* | (2006.01) |
| *A61B 8/00* | (2006.01) |
| *C07D 401/04* | (2006.01) |
| *C07D 241/20* | (2006.01) |
| *C07D 241/24* | (2006.01) |
| *C07D 241/28* | (2006.01) |
| *C07D 401/14* | (2006.01) |
| *C07D 403/04* | (2006.01) |
| *C07D 403/12* | (2006.01) |
| *C07D 403/14* | (2006.01) |
| *C07D 405/04* | (2006.01) |
| *C07D 409/04* | (2006.01) |
| *C07D 409/06* | (2006.01) |
| *C07D 409/10* | (2006.01) |
| *C07D 409/14* | (2006.01) |

(Continued)

(52) U.S. Cl.
CPC ............ *C07D 401/04* (2013.01); *C07D 241/20* (2013.01); *C07D 241/24* (2013.01); *C07D 241/28* (2013.01); *C07D 401/14* (2013.01); *C07D 403/04* (2013.01); *C07D 403/12* (2013.01); *C07D 403/14* (2013.01); *C07D 405/04* (2013.01); *C07D 409/04* (2013.01);

*C07D 409/06* (2013.01); *C07D 409/10* (2013.01); *C07D 409/14* (2013.01); *C07D 413/04* (2013.01); *C07D 417/04* (2013.01); *C07D 473/18* (2013.01); *C07D 473/34* (2013.01)

(58) Field of Classification Search
CPC . A61K 49/0004; A61K 49/00; A61K 49/001; A61K 49/0032; A61K 49/0021; A61K 41/0057; A61K 2123/00; A61K 2121/00; A61K 31/4965; A61K 31/497; A61K 31/5377; C07D 241/00; C07D 241/26; C07D 241/24; C07D 241/20; C07D 241/12; C07D 241/18; C07D 241/16; C07D 241/14; C07D 241/10; C07D 241/06; C07D 241/02; C07D 241/36; C07D 241/30; C07D 241/28; C07D 241/22; C07D 241/40; C07D 241/46; C07D 403/12; C07D 401/14; C07D 401/04; C07D 403/04; C07D 403/14; C07D 405/04; C07D 409/04; C07D 409/06; C07D 409/10; C07D 409/14; C07D 413/04; C07D 417/04; C07D 473/18; C07D 473/34
USPC ............. 424/1.11, 1.65, 1.81, 1.85, 1.89, 9.1, 424/9.2, 9.3, 9.4, 9.5, 9.6, 9.7, 9.8; 544/1, 544/120, 224, 336, 407; 514/235.8, 255.05, 514/255.06
See application file for complete search history.

(56) References Cited

U.S. PATENT DOCUMENTS 3,215,550 A * 11/1965 Strobel et al. ................. 252/588
3,814,757 A    6/1974 Donald
(Continued)

FOREIGN PATENT DOCUMENTS

CA   2 340 250   3/2000
EP   0 402 472   12/1990
(Continued)

OTHER PUBLICATIONS

Yamamoto et al., "2-Amino-3-phenylpyrazine, a sensitive fluorescence prelabeling reagent for the chromatographic or electrophoretic determination of saccharides", Journal of chromagotraphy, 2003, vol. 1004, No. 1-2, pp. 99-106, XP004436979.
(Continued)

*Primary Examiner* — D L Jones

(57) ABSTRACT

The present invention relates to pyrazine derivatives capable of absorbing and emanating spectral energy in the visible and/or near infrared spectrum. Pyrazine derivatives of the invention may be administered to a patient in the form of a pharmaceutically acceptable composition and utilized in medical (e.g., diagnostic imaging) procedures.

39 Claims, 1 Drawing Sheet

(51) Int. Cl.
*C07D 413/04* (2006.01)
*C07D 417/04* (2006.01)
*C07D 473/18* (2006.01)
*C07D 473/34* (2006.01)

(56) References Cited

U.S. PATENT DOCUMENTS

| | | | |
|---|---|---|---|
| 3,948,895 | A | 4/1976 | Donald |
| 6,440,389 | B1* | 8/2002 | Rabito ............................ 424/9.6 |
| 6,525,181 | B2* | 2/2003 | Kasada et al. ................. 534/707 |
| 7,041,672 | B2* | 5/2006 | Verhoest et al. ......... 514/255.05 |
| 7,067,506 | B2* | 6/2006 | Keegan et al. ................ 514/183 |
| 8,722,685 | B2* | 5/2014 | Rajagopalan et al. ... 514/255.06 |
| 2005/0113387 | A1 | 5/2005 | Yonishi et al. |
| 2005/0239800 | A1* | 10/2005 | Wang et al. .............. 514/255.05 |

FOREIGN PATENT DOCUMENTS

| | | |
|---|---|---|
| JP | 2017163 | 1/1990 |
| JP | 4112877 | 4/1992 |
| JP | 1997 143168 | 6/1997 |
| JP | 1997 202765 | 8/1997 |
| WO | WO 88/01264 | 2/1988 |
| WO | WO 2006/026038 | 3/2006 |

OTHER PUBLICATIONS

Luo et al., "Rapid method for the determination of ampicillin residues in animal muscle tissues by high-performance liquid chromatography with fluorescence detection", Journal of Chromatography, 1997, vol. 694, No. 2, pp. 401-407, XP004084403.

Nakamura et al., "Studies on herbicidal 2,3-dicyanopyrazines. Part II. Structure-activity relationships of herbicidal 5-ethylamino- and 5-propylamino-2,3-dicyanopyrazines", Agricultural and Biological Chemistry, 1983, vol. 47, No. 7, pp. 1561-1567.

Yozo et al., "Chemistry of diaminomaleonitrile. 5. Dihydropyrazine synthesis", J. Org. hem . . . , 1979, vol. 44, pp. 1871-4876, XP002469389.

Database CAPLUS [Online], Chemical Abstracts Service, Columbus, Ohio, US; 1934, XP002469390.

Licha et al., "Optical imaging in drug discovery and diagnostic applications", Advanced Drug Delivery Reviews, 2005, vol. 57, No. 8, pp. 1087-1108, XP004921402.

Hassan et al., "Biomedical applications of fluorescence imaging in vivo", Comparative Medicine, 2004, 54(6), pp. 635-644.

Shah et al., "Molecular optical imaging: applications leading to the development of present day therapeutics", NeuroRx, 2005, 2(2), pp. 215-225.

Solban et al., "Targeted optical imaging and photodynamic therapy", Ernst Schering Research Foundation Workshop, 2005, 49, pp. 229-258.

Jain R. K., "Barriers to Drug Delivery in Solid Tumors", Scientific American, 1994, 271, pp. 58-65.

Sekar N., "Pyrazine dyes: An update", Colourage, 1999, pp. 41-44.

Shirai et al., "Synthesis and fluorescent properties of 2,5-diamino-3,6-dicyanopyrazine dyes", Dyes and Pigments, 1998, 39, pp. 49-68.

Kim et al., "Self-assembling of aminopyrazine fluorescent dyes and their solid state spectra", Dyes and Pigments, 1998, 39, pp. 341-357.

Blanchard-Desce et al., J. Chem. Phys, 2000, 113, pp. 3951.

Kershaw, Two-Photon Absorption, Characterizations, Techniques, and Tabulations for Organic Non-Linear Optical Materials, Ch. 7, pp. 515-654 (date not provided).

Dorshow et al., "Monitoring Physiological Function by Detection of Exogenous Fluorescent Contrast Agents", Optical Diagnostics of Biological Fluids IV, Proceedings of SPIE, 1999, 3599, pp. 2-8.

Taylor et al., J. Org. Chem., 1982, 47, p. 552.

Laduree et al., Heterocycles, 1984, 22(2), pp. 299-301.

Zhang et al., "A Regioselective Synthesis of Methyl 7-Amino-3-Phenylthieno-[2,3-b]Pyrazine-6- Carboxylate", Synthetic Communications, 31(5), pp. 725-730.

Zhang et al., "A Regioselective Synthesis of Methyl 7-Amino-3-Phenylthieno-[2,3-b]Pyrazine-6-Carboxylate", Synthetic Communications, 31(5), pp. 725-730.

Yamamoto, Science of Synthesis, Category 2 Hetarenes and Related Ring Systems, vol. 16 Six-membered Hetarenes with Two Identical Heteroatoms, pp. 751-845.

* cited by examiner

PYRAZINE DERIVATIVES WITH EXTENDED CONJUGATION AND METHODS OF USING THE SAME IN OPTICAL APPLICATIONS

FIELD OF THE INVENTION

The present invention relates to pyrazine derivatives that absorb and emanate spectral energy in the visible, near infrared, and/or any other wavelength useful for optical detection in medical procedures.

BACKGROUND

As a preliminary note, various publications are referenced throughout this disclosure by Arabic numerals in brackets. Full citation corresponding to each reference number is listed following the detailed description. In other instances, the particular reference is cited in the text of the specification. In either situation, the disclosures of these publications are provided in order to describe the state of the art to which this invention pertains.

Molecules absorbing, emitting, or scattering in the visible, NIR, or long-wavelength (UV-A, >300 nm) region of the electromagnetic spectrum are useful for optical tomography, optical coherence tomography, fluorescence endoscopy, photoacoustic technology, sonofluorescence technology, light scattering technology, laser assisted guided surgery (LAGS), and phototherapy. The high sensitivity associated with fluorescence phenomenon parallels that of nuclear medicine, and permits visualization of organs and tissues without the negative effect of ionizing radiation.

Dynamic monitoring of physiological functions of patients is highly desirable in order to minimize the risk of acute organ failure, e.g., acute renal failure, brought about by various clinical, physiological, and pathological conditions (see, for example, C. A. Rabito et al., *Renal Function in Patients At Risk With Contrast Material-induced Acute Renal Failure: Noninvasive Real-Time Monitoring*, Radiology 18, 851-54 (1993)). Such dynamic monitoring is particularly important in the case of critically ill or injured patients, because a large percentage of these patients tend to face the risk of multiple organ failure (MOF), potentially resulting in death (see, for example, C. C. Baker et al., *Epidemiology of Trauma Deaths*, Amer. J. of Surgery, 144-150 (1980)). MOF is a sequential failure of the lungs, liver, and kidneys and is incited by one or more of acute lung injury, adult respiratory distress syndrome, hypermetabolism, hypotension, persistent inflammatory focus and sepsis syndrome.

Traditionally, the renal function of a patient has been determined using crude measurements of the patient's urine output and plasma creatinine levels (see, for example, P. D. Dollan et al., *A Clinical Appraisal of the Plasma Concentration and Endogenous Clearance of Creatinine*, Amer. J. Med. 32, 65-79 (1962) and Saunders, W. B., *Clinical Diagnosis and Management*, Laboratory Methods, 17th ed., Philadelphia, Pa. (1984)). These values are frequently misleading because such values are affected by age, state of hydration, renal perfusion, muscle mass, dietary intake, and many other clinical and anthropometric variables. In addition, a single value obtained several hours after sampling is difficult to correlate with other important physiologic events such as blood pressure, cardiac output, state of hydration and other specific clinical events (e.g., hemorrhage, bacteremia, ventilator settings and others).

With regard to conventional renal monitoring procedures, an approximation of a patient's glomerular filtration rate (GFR) can be made via a 24 hour urine collection procedure that (as the name suggests) typically requires about 24 hours for urine collection, several more hours for analysis, and a meticulous bedside collection technique. Unfortunately, the undesirably late timing and significant duration of this conventional procedure can reduce the likelihood of effectively treating the patient and/or saving the kidney(s). As another drawback to this type of procedure, repeat data tends to be equally as cumbersome to obtain as the originally acquired data.

Occasionally, changes in serum creatinine of a patient must be adjusted based on measurement values such as the patient's urinary electrolytes and osmolality as well as derived calculations such as "renal failure index" and/or "fractional excretion of sodium." Such adjustments of serum creatinine undesirably tend to require contemporaneous collection of additional samples of serum and urine and, after some delay, further calculations. Frequently, dosing of medication is adjusted for renal function and thus can be equally as inaccurate, equally delayed, and as difficult to reassess as the measurement values and calculations upon which the dosing is based. Finally, clinical decisions in the critically ill population are often equally as important in their timing as they are in their accuracy.

Thus, there is a need to develop improved compositions, devices and methods for measuring renal function (e.g., GFR) using non-ionizing radiation. The availability of a real-time, accurate, repeatable measure of renal excretion rate using exogenous markers under a variety of circumstances would represent a substantial improvement over any currently available or widely practiced method.

SUMMARY

The present invention relates to pyrazine derivatives that are capable of absorbing and emanating spectral energy in the visible and/or near infrared spectrum, that possess what may be characterized as extended, continuously conjugated π-systems. Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of features and aspects that may not be set forth below.

In particular, one aspect of the invention is directed to a pyrazine derivative that is substituted by at least one substituent that includes a chemically unsaturated moiety. This chemically unsaturated moiety is directly bonded to a carbon atom of the pyrazine ring or indirectly bonded to a carbon atom of the pyrazine ring through a linking moiety that is selected to permit a continuously conjugated π-system between the pyrazine and the unsaturated moiety.

In another aspect, the present invention is directed to a pyrazine derivative of Formula 1 below.

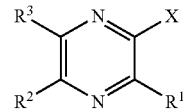

Formula 1

With regard to Formula 1, X is —Ar—Y, —C(R$^4$)=C(R$^5$)—Ar—Y, —C≡C—Ar—Y, —N=N—Ar—Y, —CO—Ar—Y, —N(R$^6$)—Ar—Y, —O—Ar—Y, —S—Ar—Y, —SO—Ar—Y, —SO$_2$—Ar—Y, —C(R$^4$)=C ($R^5$)—Y, or —C≡C—Y. For instance, in some embodiments, X may be —Ar—Y, —C($R^4$)═C($R^5$)—Ar—Y, —C≡C—Ar—Y, —N═N—Ar—Y, —CO—Ar—Y, —N($R^6$)—Ar—Y, —O—Ar—Y, —S—Ar—Y, —SO—Ar—Y, or —$SO_2$—Ar—Y. In other embodiments, X may be —Ar—Y. In still other embodiments, X may be —C($R^4$)═C($R^5$)—Ar—Y. While in yet other embodiments, X may be —N═N—Ar—Y.

Ar of Formula 1 is phenyl, biphenyl, pyridyl, pyridazyl, pyrimidinyl, pyrazinyl, pyrrolyl, furanyl, thiopheneyl, pyrazolyl, imidazolyl, oxazolyl, thiazolyl, triazinyl, triazolyl or thiadiazolyl; with the proviso that if Ar is phenyl, pyrrolyl, or thiopheneyl, then at least one of $R^1$, $R^2$, and $R^3$ is other than hydrogen. For instance, in some embodiments of the pyrazine derivative of Formula 1, Ar may be phenyl, biphenyl, pyridyl, pyrazinyl, pyrrolyl, furanyl, or thiopheneyl. In some embodiments, Ar may be phenyl, pyridyl, pyrazinyl, pyrrolyl, furanyl, or thiopheneyl. Ar of some embodiments may be phenyl, pyrrolyl, or furanyl. For example, in one embodiment, Ar is phenyl. In another embodiment, Ar is pyrrolyl. In still another embodiment, Ar is furanyl.

Y of Formula 1 is hydrogen, $C_1$-$C_{10}$ alkyl, halo, trihaloakyl, —CN, —$CO_2R^7$, —$CONR^8R^9$, —$COR^{10}$, —$NO_2$, —$SOR^{11}$, —$SO_2R^{12}$, —$SO_2OR^{13}$, —$PO_3R^{14}R^{15}$, —$OR^{16}$, —$SR^{17}$, —$NR^{18}R^{19}$, —$N(R^{20})COR^{21}$, —$P(R^{22})_3$, —CO(AA)$_j$, —CONH(PS)$_k$, or X. For instance, in some embodiments of the pyrazine derivative of Formula 1, Y may be —H, $C_1$-$C_{10}$ alkyl, halo, trihaloakyl, —CN, —$CO_2R^7$, —$CONR^8R^9$, —$COR^{10}$, —$NO_2$, —$SO_2R^{12}$, —$OR^{16}$, —$SR^{17}$, —$NR^{18}R^{19}$, —$N(R^{20})COR^{21}$, —CO(AA)$_j$, or —CONH(PS)$_k$. In some embodiments, Y may be —H, $C_1$-$C_{10}$ alkyl, halo, trihaloakyl, —CN, —$CO_2R^7$, —$CONR^8R^9$, —$OR^{16}$, —$NR^{18}R^{19}$, or —$N(R^{20})COR^{21}$. Y of some embodiments may be —H, —CN, —$CO_2R^7$, —$CONR^8R^9$, —$OR^{16}$, —$NR^{18}R^{19}$, or —$N(R^{20})COR^{21}$. For example, in one embodiment, Y may be —H, —$CO_2R^7$, —$OR^{16}$, or —$NR_{18}R^{19}$. In another embodiment, Y may simply be —H.

Still referring to Formula 1 above, each of $R^1$, $R^2$ and $R^3$ is independently hydrogen, $C_1$-$C_{10}$ alkyl, halo, trihaloakyl, —CN, —$CO_2R^7$, —$CONR^8R^9$, —$COR^{10}$, —$NO_2$, —$SOR^{11}$, —$SO_2R^{12}$, —$SO_2OR^{13}$, —$PO_3R^{14}R^{15}$, —$OR^{16}$, —$SR^{17}$, —$NR^{18}R^{19}$, —$N(R^{20})COR^{21}$, —$P(R^{22})_3$, —CO(AA)$_j$, —CONH(PS)$_k$, or X. For instance, in some embodiments, each of $R^1$ to $R^3$ is independently —H, $C_1$-$C_{10}$ alkyl, —CN, —$CO_2R^7$, —$CONR^8R^9$, —$OR^{16}$, —$SR^{17}$, —$NR^{18}R^{19}$, —CO(AA)$_j$, —CONH(PS)$_k$, or X. In some embodiments, each of $R^1$ to $R^3$ is independently —CN, —$CO_2R^7$, —$CONR^8R^9$, —$NR^{18}R^{19}$, or X. In some embodiments, each of $R^1$ to $R^3$ is independently —CN, —$CONR^8R^9$, —$NR^{18}R^{19}$, or X. In one particular embodiment, one of $R^1$, $R^2$, and $R^3$ is X, and each of the other two of $R^1$, $R^2$, and $R^3$ is independently —CN, —$CONR^8R^9$, or —$NR^{18}R^{19}$. In another particular embodiment, one of $R^1$, $R^2$, and $R^3$ is —CN, —$CONR^8R^9$, or —$NR^{18}R^{19}$; and each of the other two of $R^1$, $R^2$, and $R^3$ is X. In still another particular embodiment, each of $R^1$ and $R^3$ is independently —H, —$OR^{16}$, —$SR^{17}$, or —$NR^{18}R^{19}$, and $R^2$ is —CN, —$CO_2R^7$, —$CONR^8R^9$, —$COR^{10}$, —$SO_2R^{12}$, —CO(AA)$_j$, —CONH(PS)$_k$, or X.

As stated above, one or more of Y, $R^1$, $R^2$ and $R^3$ of Formula 1 may be —CO(AA)$_j$. In such embodiments, (AA)$_j$ is a polypeptide chain that includes the same or different natural or unnatural α-amino acids linked together by peptide bonds. For instance, in some embodiments, (AA)$_j$ may be a polypeptide chain consisting of natural α-amino acids selected from aspartic acid, asparigine, arginine, histidine, lysine, glutamic acid, glutamine, serine, and homoserine. Still referring to (AA)$_j$, j may be any appropriate integer. For instance, in some embodiments, j may be an integer from 1 to 50. In other embodiments, j may be an integer from 1 to 20.

As stated above, one or more of Y, $R^1$, $R^2$ and $R^3$ of Formula 1 may be —CONH(PS)$_k$. In such embodiments, (PS)$_k$ is a sulfated or non-sulfated polysaccharide chain comprising the same or different monosaccharide units connected together by glycosidic linkages. For instance, in some embodiments, (PS)$_k$ may be a sulfated or non-sulfated polysaccharide chain consisting of glucose, fructose, mannose, and ribose. Still referring to (PS)$_k$, k may be any appropriate integer. For instance, in some embodiments, k may be an integer from 1 to 50. In other embodiments, k may be an integer from 1 to 20.

Still referring to Formula 1, each of $R^4$ to $R^{22}$ is independently —H, $C_1$-$C_{10}$ alkyl, —$(CH_2)_aOR^{23}$, —$CH_2(CHOH)_aR^{24}$, —$CH_2(CHOH)_aCO_2H$, —$(CHCO_2H)_aCO_2H$, —$(CH_2)_aNR^{25}R^{26}$, —$CH[(CH_2)_bNH_2]_aCO_2H$, —$CH[(CH_2)_bNH_2]_aCH_2OH$, —$CH_2(CHNH_2)_aCH_2NR^{27}R^{28}$, —$(CH_2CH_2O)_cR^{29}$, or —$(CH_2)_dCO(CH_2CH_2O)_cR^{30}$. Further, each of $R^{23}$ to $R^{30}$ is independently —H or —$CH_3$. In some embodiments, each of $R^4$ to $R^{21}$ is independently —H, $C_1$-$C_{10}$ alkyl, —$(CH_2)_aOR^{23}$, —$CH_2(CHOH)_aR^{24}$, —$CH_2(CHOH)_aCO_2H$, —$(CHCO_2H)_aCO_2H$, —$(CH_2)_aNR^{25}R^{26}$, —$CH[(CH_2)_bNH_2]_aCO_2H$, —$CH[(CH_2)_bNH_2]_aCH_2OH$, —$CH_2(CHNH_2)_aCH_2NR^{27}R^{28}$, —$(CH_2CH_2O)_cR^{29}$, or —$(CH_2)_dCO(CH_2CH_2O)_cR^{30}$. For example, in some embodiments, each of $R^7$ to $R^{21}$ may independently be —H, $C_1$-$C_{10}$ alkyl, or —$(CH_2)_aOR^{23}$. In one particular embodiment, $R^7$ to $R^{21}$ may independently be —H or $C_1$-$C_{10}$ alkyl.

With regard to the substituents of the pyrazine derivatives of Formula 1, each of a, b, c, and d may be any appropriate integer. For instance, in some embodiments, each of a, b, and d may independently be an integer from 1 to 10, and c may be an integer from 1 to 100. In some embodiments, each of a, b, and d may independently be an integer from 1 to 6. In some embodiments, c may be an integer from 1 to 20.

Still another aspect of the invention is directed to a pyrazine derivative having at least one electron withdrawing group and at least one electron donating group bonded directly or indirectly to a carbon atom of the pyrazine ring. In this pyrazine derivative, one or more of the electron withdrawing and electron donating group(s) is bonded to the pyrazine ring through a resonance bond conjugating a chemically unsaturated linking moiety and the electron withdrawing or electron donating group.

Yet another aspect of the invention is directed to a pyrazine derivative of Formula 2 below.

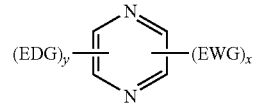

Formula 2

EWG is an electron withdrawing group, and EDG is an electron donating group. Further, at least one of EWG and EDG is conjugated to the pyrazine ring through a chemically unsaturated linking moiety. In addition, each of X and Y is independently 1, 2, or 3, where the sum of X and Y is 2, 3, or 4. For example, in some embodiments, each of X and Y may be 1. In other embodiments, each of X and Y may be 2. In such embodiments where each of X and Y is 2, the first EDG may be positioned para to the second EDG with respect to the pyrazine ring, and where the first EWG may be positioned para to the second EWG with respect to the pyrazine ring.

Still yet another aspect of the invention is directed to a pyrazine derivative of Formula 3 below.

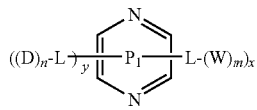

Formula 3

Each D is independently an electron donating group, and each W is independently an electron withdrawing group. Further, each m is independently a positive integer, and each n is independently a positive integer. Each L is a bond or a chemically unsaturated linking moiety conjugating D or W, respectively, to the pyrazine ring ($P_1$) by a resonance bond, provided at least one L is a chemically unsaturated linking moiety. Each of X and Y is independently 1, 2, or 3, where the sum of X and Y is 2, 3, or 4.

With regard to pyrazine derivatives of Formula 3, X and Y may each be 1 in some embodiments. In other embodiments, X and Y may each be 2. In still other embodiments, X may be 1, and Y may be 3. In yet other embodiments, X may be 3, and Y may be 1.

n and m of Formula 3 may be any appropriate numbers. For instance, in some embodiments, n may be greater than 1. As another example, in some embodiments, m may be greater than one.

Yet another aspect of the invention is directed to pharmaceutical compositions that include at least one of a pyrazine derivative described herein or a pharmaceutically acceptable salt thereof.

Still another aspect of the invention is directed to methods of using pyrazine derivatives described herein in medical (e.g., diagnostic) procedures.

Various refinements exist of the features noted above in relation to the various aspects of the present invention. Further features may also be incorporated in these various aspects as well. These refinements and additional features may exist individually or in any combination. For instance, various features discussed below in relation to one or more of the exemplary embodiments may be incorporated into any of the above-described aspects of the present invention alone or in any combination. Again, the brief summary presented above is intended only to familiarize the reader with certain aspects and contexts of the present invention without limitation to the claimed subject matter.

BRIEF DESCRIPTION OF THE FIGURES

The figures are structures of conventional visible and NIR dyes.

DETAILED DESCRIPTION OF SPECIFIC EMBODIMENTS

Figure 1A:
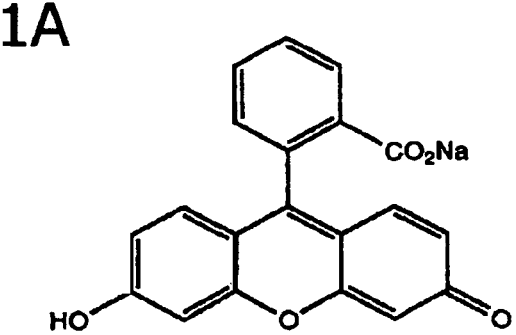
FIG. 1a depicts the chemical structure of Fluorescein $\lambda_{max}$: 496.
Figure 1B:
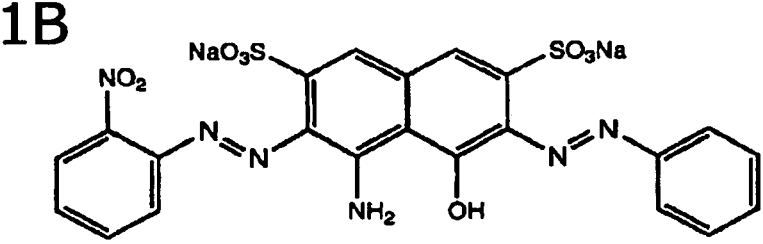
FIG. 1b depicts the chemical structure of Acid Blue $\lambda_{max}$: 602.
Figure 1C:
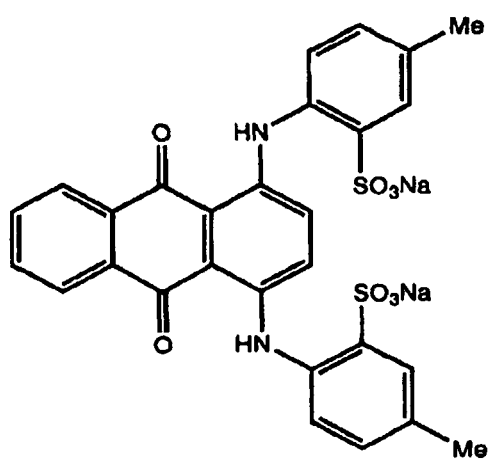
FIG. 1c depicts the chemical structure of Acid Green $\lambda_{max}$: 642.
Figure 1D:
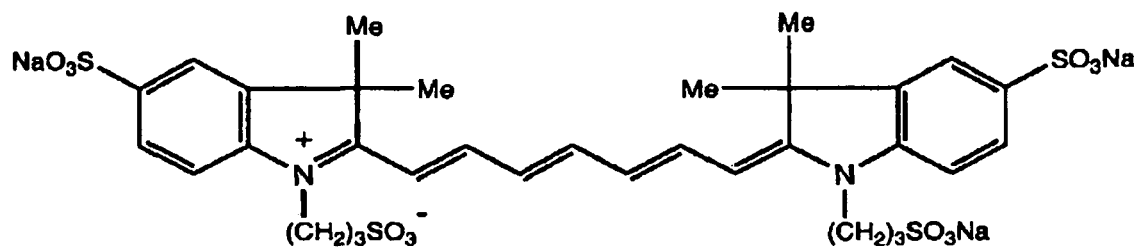
FIG. 1d depicts the chemical structure of Cyanine Tetrasulfonate $\lambda_{max}$: 670.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with regulatory-related and/or business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Pyrazines are one of the very few classes of small molecules having highly desirable photophysical properties for various biomedical and non-medical optical applications. In particular, pyrazine derivatives containing electron donating groups (sometimes abbreviated herein as EDG or EDGs) in the 2,5 positions and electron withdrawing groups (sometimes abbreviated herein as EWG or EWGs) in the 3,6 positions are shown to absorb and emit in the visible region with a large Stokes shift.

The centrosymmetric substitution pattern described herein with EDGs in the 2,5 positions and EWGs in the 3,6 positions of the pyrazine ring imparts push-pull quadrupolar character to these molecules. Semi-empirical calculations on symmetrically similar non-pyrazine analogues suggest that they have two excited states, (a) and (e), due to this quadrupolar disposition of donor and acceptor functionality [9]. The symmetric intramolecular charge transfer involving the two EDG-EWG pairs is responsible for the enhancement of a two-photon cross-section and one- and two-photon bathochromic shifts in these compounds. One-photon absorption is allowed between the ground state and (a) because they have opposite symmetry. Two-photon absorption is allowed between the ground state and (e) because they have the same symmetry. Two-photon absorption is particularly useful for optical imaging and tomography methods in that it is based upon the simultaneous absorption of two low energy photons by these pyrazine fluorophores in a single quantum event to induce the excitation normally accomplished by a single high-energy photon. The resulting high spatial localization of this excitation event is due to the quadratic relation between excitation and illumination intensity. Thus, fluorescence only occurs at the beam focus and with the eventual use of ultrafast, pulsed, near-IR lasers, deeper tissue imaging with less photobleaching will be possible [10].

At least some pyrazine derivatives of the invention may be characterized as having a pyrazine core substituted by at least one substituent comprising a chemically unsaturated moiety, the unsaturated moiety being directly bonded to a carbon atom of the pyrazine ring or indirectly bonded to a carbon atom of the pyrazine ring through a linking moiety, the linking moiety being selected to permit a continuously conjugated π-system between the pyrazine and the unsaturated moiety.

Some pyrazine derivatives of the invention are of Formula 1 below,

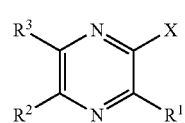

Formula 1 where X is selected from the group consisting of —Ar—Y, —C($R^4$)=C($R^5$)—Ar—Y, —C≡C—Ar—Y, —N=N—Ar—Y, —CO—Ar—Y, —N($R^6$)—Ar—Y, —O—Ar—Y, —S—Ar—Y, —SO—Ar—Y, —$SO_2$—Ar—Y, —C($R^4$)=C($R^5$)—Y, and —C≡C—Y. Ar is an aryl or heteroaryl moiety selected from the group consisting of phenyl, biphenyl, pyridyl, pyridazyl, pyrimidinyl, pyrazinyl, pyrrolyl, furanyl, thiopheneyl, pyrazolyl, imidazolyl, oxazolyl, thiazolyl, triazinyl, triazolyl and thiadiazolyl; with the proviso that if Ar is phenyl, pyrrolyl, or thiopheneyl, then at least one of $R^1$, $R^2$, and $R^3$ is other than hydrogen. Y and $R^1$ to $R^3$ may independently be hydrogen or electron donating or electron withdrawing groups selected from the group consisting of $C_1$-$C_{10}$ alkyl, halo, trihaloakyl, —CN, —$CO_2R^7$, —$CONR^8R^9$, —$COR^{10}$, —$NO_2$, —$SOR^{11}$, —$SO_2R^{12}$, —$SO_2OR^{13}$, —$PO_3R^{14}R^{15}$, —$OR^{16}$, —$SR^{17}$, —$NR^{18}R^{19}$, —$N(R^{20})COR^{21}$, —$P(R^{22})_3$, —CO(AA)$_j$, —CONH(PS)$_k$, and X. (AA)$_j$ is a polypeptide chain comprising the same or different natural or unnatural α-amino acids linked together by peptide bonds, where 'j' is 1 to 50. (PS)$_k$ is a sulfated or non-sulfated polysaccharide chain comprising the same or different monosaccharide units connected together by glycosidic linkages, where 'k' is 1 to 50. Each of the R groups of $R^4$ to $R^{22}$ is independently selected from the group consisting of —H, $C_1$-$C_{10}$ alkyl, —$(CH_2)_aOR^{23}$, —$CH_2(CHOH)_aR^{24}$, —$CH_2(CHOH)_aCO_2H$, —$(CHCO_2H)_aCO_2H$, —$(CH_2)_aNR^{25}R^{26}$, —$CH[(CH_2)_bNH_2]_aCO_2H$, —$CH[(CH_2)_bNH_2]_aCH_2OH$, —$CH_2(CHNH_2)_aCH_2NR^{27}R^{28}$, —$(CH_2CH_2O)_cR^{29}$, and —$(CH_2)_dCO(CH_2CH_2O)_cR^{30}$. Each of the R groups of $R^{23}$ to $R^{30}$ is independently —H or —$CH_3$. The subscripts 'a', 'b', and 'd' are independently 1 to 10, and 'c' is 1 to 100. In some embodiments of the invention, the selection of one or more R groups of $R^1$ to $R^{30}$ may be dependent on the selection of one or more of the other R groups of $R^1$ to $R^{30}$. In other embodiments, the selection of each of the R groups of $R^1$ to $R^{50}$ may be independent of the other selected R groups of $R^1$ to $R^{30}$.

In one pyrazine derivative represented by Formula 1, X is selected from the group consisting of —Ar—Y, —C($R^4$)=C($R^5$)—Ar—Y, —C≡C—Ar—Y, —N=N—Ar—Y, —CO—Ar—Y, —N($R^6$)—Ar—Y, —O—Ar—Y, —SO—Ar—Y, and —$SO_2$—Ar—Y. Ar is selected from the group consisting of phenyl, biphenyl, pyridyl, pyrazinyl, pyrrolyl, furanyl, and thiopheneyl; with the proviso that if Ar is phenyl, pyrrolyl, or thiopheneyl, then at least one of $R^1$, $R^2$, and $R^3$ is other than hydrogen. Y is selected from the group consisting of —H, $C_1$-$C_{10}$ alkyl, halo, trihaloakyl, —CN, —$CO_2R^7$, —$CONR^8R^9$, —$COR^{10}$, —$NO_2$, —$SO_2R^{12}$, —$OR^{16}$, —$SR^{17}$, —$NR^{18}R^{19}$, —$N(R^{20})COR^{21}$, —CO(AA)$_j$, and —CONH(PS)$_k$. $R^1$ and $R^3$ are independently selected from the group consisting of —H, —$OR^{16}$, —$SR^{17}$, and —$NR^{18}R^{19}$. $R^2$ is selected from the group consisting of —CN, —$CO_2R^7$, —$CONR^8R^9$, —$COR^{10}$, —$SO_2R^{12}$, —CO(AA)$_j$, —CONH(PS)$_k$, and X. (AA)$_j$ is a polypeptide chain comprising the same or different natural or unnatural α-amino acids linked together by peptide bonds, where 'j' is 1 to 50. (PS)$_k$ is a sulfated or non-sulfated polysaccharide chain comprising the same or different monosaccharide units connected together by glycosidic linkages, where 'k' is 1 to 50. Each of the R groups of $R^4$ to $R^{21}$ is independently selected from the group consisting of —H, $C_1$-$C_{10}$ alkyl, —$(CH_2)_8OR^{23}$, —$CH_2(CHOH).R^{24}$, —$CH_2(CHOH)_aCO_2H$, —$(CHCO_2H)_aCO_2H$, $(CH_2)_aNR^{25}R^{26}$, —$CH[(CH_2)_bNH_2]_aCO_2H$, —$CH[(CH_2)_bNH_2]_aCH_2OH$, —$CH_2(CHNH_2)_aCH_2NR^{27}R^{28}$, —$(CH_2CH_2O)_cR^{29}$, and —$(CH_2)_dCO(CH_2CH_2O)_cR^{30}$. Each of the R groups of $R^{23}$ to $R^{30}$ is independently —H or —$CH_3$. In some instances, the amino acids comprising (AA)$_j$ are selected from the group consisting of aspartic acid, asparigine, arginine, histidine, lysine, glutamic acid, glutamine, serine, and homoserine and the monosaccharide units of (PS)$_k$ are selected from the group consisting of glucose, fructose, mannose, and ribose. The subscripts 'a', 'b', and 'd' are independently 1 to 6, 'c' is 1 to 20, and 'j' and 'k' are independently 1 to 20.

In another pyrazine derivative represented by Formula 1, X is selected from the group consisting of —Ar—Y, —C($R^4$)=C($R^5$)—Ar—Y, —C≡C—Ar—Y, —N=N—Ar—Y, —CO—Ar—Y, —Ar—Y. Ar is selected from the group consisting of phenyl, biphenyl, pyridyl, pyrazinyl, pyrrolyl, furanyl, and thiopheneyl; with the proviso that if Ar is phenyl, pyrrolyl, or thiopheneyl, then at least one of $R^1$, $R^2$, and $R^3$ is other than hydrogen. Y is selected from the group consisting of —H, $C_1$-$C_{10}$ alkyl, halo, trihaloakyl, —CN, —$CO_2R^7$, —$CONR^8R^9$, —$COR^{10}$, —$NO_2$, —$SO_2R^{12}$, —$OR^{16}$, —$SR^{17}$, —$NR^{18}R^{19}$, —$N(R^{20})COR^{21}$, —CO(AA)$_j$, and —CONH(PS)$_k$. $R^2$ is selected from the group consisting of —H, —$OR^{16}$, —$SR^{17}$, and —$NR^{18}R^{19}$. $R^1$ and $R^3$ are independently selected from the group consisting of —H, —CN, —$CO_2R^7$, —$CONR^8R^9$, —$COR^{10}$, —$SO_2R^{12}$, —CO(AA)$_j$, —CONH(PS)$_k$, and X. (AA)$_j$ is a polypeptide chain comprising the same or different natural or unnatural α-amino acids linked together by peptide bonds, wherein 'j' is 1 to 50. (PS)$_k$ is a sulfated or non-sulfated polysaccharide chain comprising the same or different monosaccharide units connected together by glycosidic linkages, wherein 'k' is 1 to 50. Each of the R groups of $R^4$ to $R^{21}$ is independently selected from the group consisting of —H, $C_1$-$C_{10}$ alkyl, —$(CH_2)_aOR^{23}$, —$CH_2(CHOH)_aR^{24}$, —$CH_2(CHOH)_aCO_2H$, —$(CHCO_2H)_aCO_2H$, —$(CH_2)_aNR^{25}R^{26}$, —$CH[(CH_2)_aNH_2]_aCO_2H$, —$CH[(CH_2)_aNH_2]_aCH_2OH$, —$CH_2(CHNH_2)_aCH_2NR^{27}R^{28}$, —$(CH_2CH_2O)_cR^{29}$, and —$(CH_2)_dCO(CH_2CH_2O)_cR^{30}$. Each of the R groups of $R^{23}$ to $R^{30}$ is independently —H or —$CH_3$.

In some instances of this embodiment, the polypeptide chain (AA)$_j$ consists of amino acids selected from the group consisting of aspartic acid, asparigine, arginine, histidine, lysine, glutamic acid, glutamine, serine, and homoserine. Typically, the polysaccharide chain (PS)$_k$ consists of glucose, fructose, mannose, and ribose units. The subscripts 'a', 'b', and 'd' are independently 1 to 6, 'c' is 1 to 20, and 'j' and 'k' are independently 1 to 20.

In another pyrazine derivative represented by Formula 1, X is selected from the group consisting of —C($R^4$)=C($R^5$)—Y and Y is selected from the group consisting of —H, $C_1$-$C_{10}$ alkyl, halo, trihaloakyl, —CN, —$CO_2R^7$, —$CONR^8R^9$, —$COR^{10}$, —$NO_2$, —$SO_2R^{12}$, —$OR^{16}$, —$SR^{17}$, —$NR^{18}R^{19}$), —$N(R^{20})COR^{21}$, —CO(AA)$_j$, and —CONH(PS)$_k$. $R^1$ and $R^3$ are independently selected from the group consisting of —H, —$OR^{16}$, —$SR^{17}$, and —$NR^{18}R^{19}$. $R^2$ is a selected from the group consisting of —H, —CN, —$CO_2R^7$, —$CONR^8R^9$, —$COR^{10}$, —$SO_2R^{12}$, —CO(AA)$_j$, —CONH (PS)$_k$, and X. Ar is selected from the group consisting of phenyl, biphenyl, pyridyl, pyrazinyl, pyrrolyl, furanyl, and thiopheneyl; with the proviso that if Ar is phenyl, pyrrolyl, or thiopheneyl, then at least one of $R^1$, $R^2$, and $R^3$ is other than hydrogen. (AA)$_j$ is a polypeptide chain comprising the same or different natural or unnatural α-amino acids linked together by peptide bonds, where 'j' is 1 to 50. Typically, the amino acids are selected from aspartic acid, asparigine, arginine, histidine, lysine, glutamic acid, glutamine, serine, and homoserine. (PS)$_k$ is a sulfated or non-sulfated polysaccharide chain comprising the same or different monosaccharide units connected together by glycosidic linkages, where 'k' is 1 to 50. Typically, the monosaccharide units are selected from glucose, fructose, mannose, and ribose. Each of the R groups of $R^4$ to $R^{21}$ is independently selected from the group consisting of —H, $C_1$-$C_{10}$ alkyl, —$(CH_2)_aOR^{23}$, —$CH_2(CHOH)_aR^{24}$, —$CH_2(CHOH)_aCO_2H$, —$(CHCO_2H)_aCO_2H$, —$(CH_2)_aNR^{25}R^{26}$, —$CH[(CH_2)_bNH_2]_aCO_2H$, —$CH[(CH_2)_bNH_2]_aCH_2OH$, —$CH_2(CHNH_2)_aCH_2NR^{27}R^{28}$, —$(CH_2CH_2O)_cR^{29}$, and —$(CH_2)_dCO(CH_2CH_2O)_cR^{30}$. Each of the R groups of $R^{23}$ to $R^{30}$ is independently —H or —$CH_3$. The subscripts 'a', 'b', and 'd' are independently 1 to 6, 'c' is 1 to 20, and 'j' and 'k' are independently 1 to 20.

In another pyrazine derivative represented by Formula 1, X is selected from the group consisting of —$C(R^4)$=$C(R^5)$—Y and —C≡C—Y. Y is selected from the group consisting of —H, $C_1$-$C_{10}$ alkyl, halo, trihaloakyl, —CN, —$CO_2R^7$, —$CONR^8R^9$, —$COR^{10}$, —$NO_2$, —$SO_2R^{12}$, —$OR^{16}$, —$SR^{17}$, —$NR^{18}R^{19}$, —$N(R^{20})COR^{21}$, —$CO(AA)_j$, and —$CONH(PS)_k$. $R^2$ is selected from the group consisting of —H, —$OR^{16}$, —$SR^{17}$, and —$NR^{18}R^{19}$. $R^1$ and $R^3$ are independently selected from the group consisting of —H, —CN, —$CO_2R^7$, —$CONR^8R^9$, —$COR^{10}$, —$SO_2R^{12}$, —$CO(AA)_j$, —$CONH(PS)_k$, and X. Ar is selected from the group consisting of phenyl, biphenyl, pyridyl, pyrazinyl, pyrrolyl, furanyl, and thiopheneyl; with the proviso that if Ar is phenyl, pyrrolyl, or thiopheneyl, then at least one of $R^1$, $R^2$, and $R^3$ is other than hydrogen. $(AA)_j$ is a polypeptide chain comprising the same or different natural or unnatural α-amino acids linked together by peptide bonds, where 'j' is 1 to 50. $(PS)_k$ is a sulfated or non-sulfated polysaccharide chain comprising the same or different monosaccharide units connected together by glycosidic linkages, where 'k' is 1 to 50. Each of the R groups of $R^4$ to $R^{21}$ is independently selected from the group consisting of —H, $C_1$-$C_{10}$ alkyl, —$(CH_2)_aOR^{23}$, —$CH_2(CHOH)_aR^{24}$, —$CH_2(CHOH)_aCO_2H$, —$(CHCO_2H)_aCO_2H$, —$(CH_2)_aNR^{25}R^{26}$, —$CH[(CH_2)_bNH_2]_aCO_2H$, —$CH[(CH_2)_bNH_2]_aCH_2OH$, —$CH_2(CHNH_2)_aCH_2NR^{27}R^{28}$, —$(CH_2CH_2O)_cR^{29}$, and —$(CH_2)_dCO(CH_2CH_2O)_cR^{30}$. Each of the R groups of $R^{23}$ to $R^{30}$ is independently —H or —$CH_3$. The amino acids comprising $(AA)_j$ are typically selected from the group consisting of aspartic acid, asparigine, arginine, histidine, lysine, glutamic acid, glutamine, serine, and homoserine. The polysaccharide units comprising $(PS)_k$ are typically selected from the group consisting of glucose, fructose, mannose, and ribose. The subscripts 'a', 'b', and 'd' are independently 1 to 6, 'c' is 1 to 20, and 'j' and 'k' are independently 1 to 20.

In another pyrazine derivative represented by Formula 1, X is selected from the group consisting of —Ar—Y, —$C(R^4)$=$C(R^5)$—Ar—Y, —C≡C—Ar—Y, and —N=N—Ar—Y. Ar is selected from the group consisting of phenyl, biphenyl, pyridyl, pyrazinyl, pyrrolyl, furanyl, and thiopheneyl; with the proviso that if Ar is phenyl, pyrrolyl, or thiopheneyl, then at least one of $R^1$, $R^2$, and $R^3$ is other than hydrogen. Y is —H, $C_1$-$C_{10}$ alkyl, halo, trihaloakyl, —CN, —$CO_2R^7$, —$CONR^8R^9$, —$OR^{16}$, —$NR^{18}R^{19}$, and —$N(R^{20})COR^{21}$. $R^1$ and $R^3$ are independently selected from the group consisting of —H, —$OR^{16}$, —$SR^{17}$, and —$NR^{18}R^{19}$. $R^2$ is a selected from the group consisting of —H, —CN, —$CO_2R^7$, —$CONR^8R^9$, —$CO(AA)_j$, —$CONH(PS)_k$, and X. Each of the R groups of $R^4$ to $R^{21}$ is independently selected from the group consisting of —H, $C_1$-$C_{10}$ alkyl, —$(CH_2)_aOR^{23}$, —$CH_2(CHOH)_aR^{24}$, —$CH_2(CHOH)_aCO_2H$, —$(CHCO_2H)_aCO_2H$, —$(CH_2)_aNR^{25}R^{26}$, —$CH[(CH_2)_bNH_2]_aCO_2H$, —$CH[(CH_2)_bNH_2]_aCH_2OH$, —$CH_2(CHNH_2)_aCH_2NR^{27}R^{28}$, —$(CH_2CH_2O)_cR^{29}$, and —$(CH_2)_dCO(CH_2CH_2O)_cR^{39}$. Each of the R groups of $R^{23}$ to $R^{30}$ is independently —H or —$CH_3$. $(AA)_j$ is a polypeptide chain consisting of natural α-amino acids selected from the group consisting of aspartic acid, glutamic acid, serine, and homoserine. $(PS)_k$ is a sulfated or non-sulfated polysaccharide chain consisting of glucose and fructose. The subscripts 'a', 'b', and 'd' are independently 1 to 6, 'c' is 1 to 20, and 'j' and 'k' are independently 1 to 20.

In another pyrazine derivative represented by Formula 1, X is selected from the group consisting of —Ar—Y, —$C(R^4)$=$C(R^5)$—Ar—Y, —C≡C—Ar—Y, and —N=N—Ar—Y. Ar is selected from the group consisting of phenyl, biphenyl, pyridyl, pyrazinyl, pyrrolyl, furanyl, and thiopheneyl; with the proviso that if Ar is phenyl, pyrrolyl, or thiopheneyl, then at least one of $R^1$, $R^2$, and $R^3$ is other than hydrogen. Y is —H, $C_1$-$C_{10}$ alkyl, halo, trihaloakyl, —CN, —$CO_2R^7$, —$CONR^8R^9$, —$OR^{16}$, —$NR^{18}R^{19}$, and —$N(R^{20})COR^{21}$. $R^2$ is selected from the group consisting of —H, —$OR^{16}$, —$SR^{17}$, and —$NR^{18}R^{19}$. $R^1$ and $R^3$ are independently selected from the group consisting of —H, —CN, —$CO_2R^7$, —$CONR^8R^9$, —$CO(AA)_j$, —$CONH(PS)_k$, and X. Each of the R groups of $R^4$ to $R^{21}$ is independently selected from the group consisting of —H, $C_1$-$C_{10}$ alkyl, —$(CH_2)_aOR^{23}$, —$CH_2(CHOH)_aR^{24}$, —$CH_2(CHOH)_aCO_2H$, —$(CHCO_2H)_aCO_2H$, —$(CH_2)_aNR^{25}R^{26}$, —$CH[(CH_2)_bNH_2]_aCO_2H$, —$CH[(CH_2)_bNH_2]_aCH_2OH$, —$CH_2(CHNH_2)_aCH_2NR^{27}R^{28}$, —$(CH_2CH_2O)_cR^{29}$, and —$(CH_2)_dCO(CH_2CH_2O)_cR^{30}$. Each of the R groups of $R^{23}$ to $R^{30}$ is independently —H or —$CH_3$. $(AA)_j$ is a polypeptide chain consisting of natural α-amino acids selected from the group consisting of aspartic acid, glutamic acid, serine, and homoserine. $(PS)_k$ is a sulfated or non-sulfated polysaccharide chain consisting of glucose and fructose. The subscripts 'a', 'b', and 'd' are independently 1 to 6, 'c' is 1 to 20, and 'j' and 'k' are independently 1 to 20.

In another pyrazine derivative represented by Formula 1, X is selected from the group consisting of —Ar—Y, —$C(R^4)$=$C(R^5)$—Ar—Y, —C≡C—Ar—Y, and —N=N—Ar—Y. Ar is selected from the group consisting of phenyl, biphenyl, pyridyl, pyrazinyl, pyrrolyl, furanyl, and thiopheneyl; with the proviso that if Ar is phenyl, pyrrolyl, or thiopheneyl, then at least one of $R^1$, $R^2$, and $R^3$ is other than hydrogen. Y is —H, $C_1$-$C_{10}$ alkyl, halo, trihaloakyl, —CN, —$CO_2R^7$, —$CONR^8R^9$, —$OR^{16}$, —$NR^{18}R^{19}$, and —$N(R^{20})COR^{21}$. $R^1$ and $R^3$ are independently —H, or —$NR^{18}R^{19}$. $R^2$ is a selected from the group consisting of —H, —CN, —$CO_2R^7$, —$CONR^8R^9$, —$CO(AA)_j$, —$CONH(PS)_k$, and X. Each of the R groups of $R^7$ to $R^{21}$ is independently —H, $C_1$-$C_{10}$ alkyl, or —$(CH_2)_aOR^{23}$. $R^{23}$ is —H or —$CH_3$. The subscripts 'a', 'j', and 'k' are independently 1 to 20.

In another pyrazine derivative represented by Formula 1, X is selected from the group consisting of —Ar—Y, —$C(R^4)$=$C(R^8)$—Ar—Y, —C≡C—Ar—Y, and —N=N—Ar—Y. Ar is selected from the group consisting of phenyl, biphenyl, pyridyl, pyrazinyl, pyrrolyl, furanyl, and thiopheneyl; with the proviso that if Ar is phenyl, pyrrolyl, or thiopheneyl, then at least one of $R^1$, $R^2$, and $R^3$ is other than hydrogen. Y is —H, $C_1$-$C_{10}$ alkyl, halo, trihaloakyl, —CN, —$CO_2R^7$, —$CONR^8R^9$, —$OR^{16}$, —$NR^{18}R^{19}$, and —$N(R^{20})COR^{21}$. $R^2$ is —H or —$NR^{18}R^{19}$. $R^1$ and $R^3$ are independently selected from the group consisting of —H, —CN, —$CO_2R^7$, —$CONR^8R^9$, —$CO(AA)_j$, —$CONH(PS)_k$, and X. Each of the R groups of $R^7$ to $R^{21}$ is independently —H, $C_1$-$C_{10}$ alkyl, or —$(CH_2)_aOR^{23}$. $R^{23}$ is —H or —$CH_3$. The subscripts 'a', 'j', and 'k' are independently 1 to 20.

In another pyrazine derivative represented by Formula 1, X is selected from the group consisting of —$C(R^4)$=$C(R^5)$—Y, Y is —H, $C_1$-$C_{10}$ alkyl, —CN, —$CO_2R^7$, and —$CONR^8R^9$. $R^1$ and $R^3$ are independently —H or —$NR^{18}R^{19}$. $R^2$ is a selected from the group consisting of —H, —CN, —$CO_2R^7$, —$CONR^8R^9$, —$CO(AA)_j$, and —$CONH(PS)_k$, and X. Ar is selected from the group consisting of phenyl, biphenyl, pyridyl, pyrazinyl, pyrrolyl, furanyl, and thiopheneyl; with the proviso that if Ar is phenyl, pyrrolyl, or thiopheneyl, then at least one of $R^1$, $R^2$, and $R^3$ is other than hydrogen. Each of the R groups of $R^7$ to $R^{21}$ is independently —H, $C_1$-$C_{10}$ alkyl, or —$(CH_2)_a R^{23}$. The subscripts 'a', 'j', and 'k' independently vary from 1 to 20.

In another embodiment of the invention represented by Formula 1, X is selected from the group consisting of —C($R^4$)=C($R^8$)—Y and —C≡C—Y. Y is —H, $C_1$-$C_{10}$ alkyl, —CN, —$CO_2R^7$, and —$CONR^8R^9$. $R^2$ is —H or —$NR^{18}R^{19}$. $R^1$ and $R^3$ are independently selected from the group consisting of —H, —CN, —$CO_2R^7$, —$CONR^8R^9$, —$CO(AA)_j$, —$CONH(PS)_k$, and X. Ar is selected from the group consisting of phenyl, biphenyl, pyridyl, pyrazinyl, pyrrolyl, furanyl, and thiopheneyl; with the proviso that if Ar is phenyl, pyrrolyl, or thiopheneyl, then at least one of $R^1$, $R^2$, and $R^3$ is other than hydrogen. Each of the R groups of $R^7$ to $R^{21}$ is independently —H, $C_1$-$C_{10}$ alkyl, or —$(CH_2)_a OR^{23}$. $R^{23}$ is —H or —$CH_3$. The subscripts 'a', 'j', and 'k' are independently 1 to 20.

Some pyrazine derivatives of the invention have at least one electron withdrawing group and at least one electron donating group bonded directly or indirectly to a carbon atom of a pyrazine core molecule where one or more of the electron withdrawing and electron donating group(s) are bonded to the pyrazine ring through a resonance bond conjugating a chemically unsaturated linking moiety and the electron withdrawing or electron donating group. Such pyrazine derivatives may be represented by Formula 2 below:

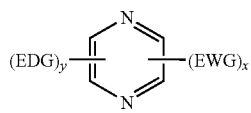

Formula 2 where EWG is an electron withdrawing group, EDG is an electron donating group, X is 1-3, Y is 1-3 and the sum of X and Y is 2-4 where at least one of EWG and EDG is conjugated to the pyrazine ring through a chemically unsaturated linking moiety. While the EWG and EDG are depicted in Formula 2 as single groups, multiple electron withdrawing groups and/or electron donating groups on each substituent arm of the pyrazine ring are contemplated by this invention. For example, one EWG arm may comprise two, three, or more electron withdrawing groups bonded to the pyrazine core via a common chemically unsaturated linking moiety.

The electron withdrawing group(s) and the electron donating group(s) of Formula 2 may be positioned ortho, meta, or para to each other with respect to the pyrazine ring. Thus, for example, the following representative substitution patterns on the pyrazine ring are contemplated by this invention when X and Y are both 1:

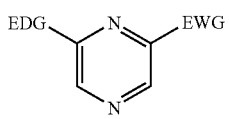

(a)

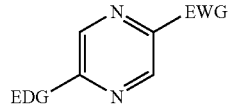

(b)

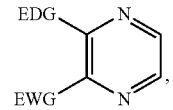

(c)

Similarly, in another embodiment, X is 1, and Y is 2. Representative pyrazine derivatives of this embodiment include the following (each EDG may be independently selected):

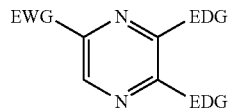

(d)

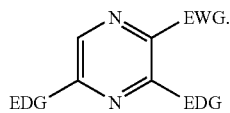

(e)

In another embodiment, X is 1, and Y is 3. Representative pyrazine derivatives of this embodiment include the following (each EDG may be independently selected):

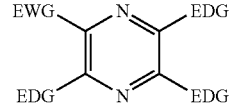

(f)

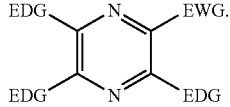

(g)

In another embodiment of Formula (I), X is 2, and Y is 1. Representative pyrazine derivatives of this embodiment include the following (each EWG may be independently selected):

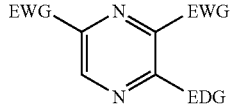

(h)

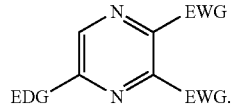

(i)

In another embodiment of Formula 2, X is 3, and Y is 1. Representative pyrazine derivatives of this embodiment include the following (each EWG may be independently selected):

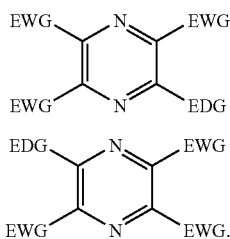

In yet another embodiment of Formula 2, X is 2, and Y is 2. Representative pyrazine derivatives of this embodiment include the following (each EWG and EDG may be independently selected):

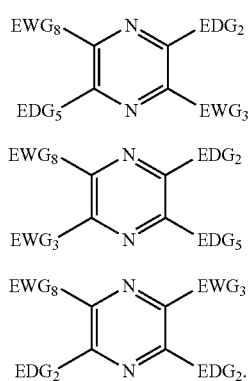

In one embodiment of Formula 2, the pyrazine derivative has the (l) substitution pattern. Specifically, two electron withdrawing groups are positioned para to each other on the pyrazine ring and two electron donating groups are positioned para to each other on the pyrazine ring. In some instances of this embodiment, the EWGs and the EDGs are selected to make the overall compound symmetrical.

The electron withdrawing group of Formula 2 may be any chemical group that draws electrons away from a reaction center. Conversely, the electron donating group of Formula 2 may be any chemical group that releases electrons into a reaction center. The chemically unsaturated linking moiety of Formula 2 may be any unsaturated group that conjugates an electron withdrawing group or electron donating group to the pyrazine ring by a resonance bond.

Some pyrazine derivatives of the invention correspond to Formula 3 below, wherein:

Formula 3

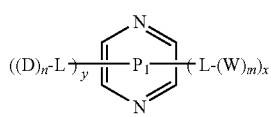

each D is independently an electron donating group;
each W is independently an electron withdrawing group;
each m is independently a positive integer;
each n is independently a positive integer;
each L is a bond or a chemically unsaturated linking moiety conjugating D or W, respectively, to the pyrazine ring, $P_1$, by a resonance bond, provided at least one L is a chemically unsaturated linking moiety; and X and Y are independently 1-3 where the sum of X and Y is 2-4.

As with Formula 2 above, the electron withdrawing group(s) and the electron donating group(s) of Formula 3 may be positioned ortho, meta, or para to each other with respect to the pyrazine ring. Thus, in one embodiment, X is 1, and Y is 1. In another embodiment, X is 1, and Y is 2. In a third embodiment, X is 1, and Y is 3. In another embodiment, X is 2, and Y is 1. In yet another embodiment, X is 2, and Y is 2. In still another embodiment, X is 3, and Y is 1. In one embodiment of Formula 3, the pyrazine derivative has a substitution pattern where two electron withdrawing groups are positioned para to each other on the pyrazine ring, and two electron donating groups are positioned para to each other on the pyrazine ring.

The m and n integers may be the same or different. In some instances, for example, there may be more EDG pyrazine arms than EWG pyrazine arms (e.g., y>x). Under these circumstances, it may be advantageous to have more EWGs on each pyrazine arm such that m is greater than n. In this manner, the overall electron donating/electron withdrawing push and pull remains relatively equal. In other instances, however, there may be a disparity between the number of EDGs and EWGs with no effort to balance the push and pull effect.

Electron Withdrawing Groups

As depicted in Formula 3 above, an electron withdrawing group is typically located at the terminus of a substituent arm of the pyrazine derivative. Typically, the electron withdrawing group(s) for Formula 2 and 3 are independently selected from cyano (—CN), carboxylates (—$CO_2R_1$), carbamates (—$CONR_2R_3$), acyl (—$COR_4$), nitro (—$NO_2$), sulfinyl (—$SOR_5$), sulfonyl (—$SO_2R_6$), —$SO_2OR_7$, and —$PO_3R_8R_9$ wherein $R_1$-$R_9$ are independently selected to enhance biological and/or physiochemical properties of the pyrazine derivative. In some instances, $R_1$-$R_9$ are independently selected from any one of a hydrogen atom, an anionic functional group (e.g., carboxylate, sulfonate, sulfate, phopshonate and phosphate) and a hydrophilic functional group (e.g., hydroxyl, carboxyl, sulfonyl, sulfonato and phosphonato). In other instances, $R_1$-$R_9$ are independently selected from hydrogen, $C_{1-10}$alkyl, aryl, heteroaryl, —$(CH_2)_a$OH, —$(CH_2)_a CO_2H$, —$(CH_2)_a SO_3H$, —$(CH_2)_a SO_3^-$, —$(CH_2)_a OSO_3H$, —$(CH_2)_a OSO_3^-$, —$(CH_2)_a NHSO_3H$, —$(CH_2)_a NHSO_3^-$, —$(CH_2)_a PO_3H_2$, —$(CH_2)_a PO_3H^-$, —$(CH_2)_a PO_3^=$, —$(CH_2)_a OPO_3H_2$, —$(CH_2)_a PO_3H^-$ and —$(CH_2)_a OPO_3$ where a is an integer from 1 to 10.

In one example of this embodiment, the EWG(s) are independently selected from —CN, —$CO_2R_1$, —$CONR_2R_3$, —$NO_2$, and —$SO_2R_6$.

Electron Donating Groups

As depicted in Formula 3 above, an electron donating group is typically located at the terminus of a substituent arm of the pyrazine derivative. Typically, the electron donating group(s) for Formula 2 and 3 are independently selected from —$OR_{10}$, —$SR_{11}$, —$NR_{12}R_{13}$, —$N(R_{14})COR_{15}$, and —$P(R_{16})$ wherein $R_{10}$-$R_{16}$ are independently selected to enhance biological and/or physiochemical properties of the pyrazine derivative. In some instances, $R_{10}$-$R_{16}$ are independently selected from any one of a hydrogen atom, an anionic functional group (e.g., carboxylate, sulfonate, sulfate, phopshonate and phosphate) and a hydrophilic functional group (e.g., hydroxyl, carboxyl, sulfonyl, sulfonato and phosphonato). In other instances, $R_{10}$-$R_{16}$ are independently selected from hydrogen, $C_1$-$C_{10}$alkyl, aryl, heteroaryl, —$(CH_2)_a$OH, —$(CH_2)_a CO_2H$, —$(CH_2)_a SO_3H$, —$(CH_2)_a SO_3^-$, —$(CH_2)_a OSO_3H$, —$(CH_2)_a OSO_3^-$, —$(CH_2)_2 NHSO_3H$, —$(CH_2)_aNHSO_3^-$, —$(CH_2)_aPO_3H_2$, —$(CH_2)_aPO_3H^-$, —$(CH_2)_aPO_3^-$, —$(CH_2)_aOPO_3H_2$, —$(CH_2)_aOPO_3H^-$ and —$(CH_2)_aOPO_3$ where a is an integer from 1 to 10.

In one example of this embodiment, the EDG(s) are independently selected from —$OR_{10}$, —$SR_{11}$, —$NR_{12}R_{13}$, and —$N(R_{14})COR_{15}$.

Linking Moieties

As described above, at least one of the substituent arms of the pyrazine derivative comprises a chemically unsaturated linking moiety conjugating an electron withdrawing group and at least one of the substituent arms of the pyrazine derivative comprises a chemically unsaturated linking moiety conjugating an electron donating group to a carbon atom of the pyrazine ring by a resonance bond. Typical unsaturated linking moieties include alkenyl, alkynyl, aryl, heteroaryl, anilino (-Ph-NH—), and azo (—NH=NH—) groups. In addition, the linking moieties may be substituted with one or more chemical groups designed to enhance the biological and/or physiochemical properties of the pyrazine derivative.

The linking moieties may be the same or different for each substituent arm of the pyrazine derivative. For example, a first linking moiety may be phenyl while another is heteroaryl. Often, however, the linking moieties will be selected to make the pyrazine derivative, as a whole, symmetrical.

In addition, more than one EWG or EDG may be bonded to the same linking moiety. Thus, for example, when the linking moiety is selected to be phenyl, a first EWG may be bonded to the phenyl ring at the position pare to the ring carbon at the point of attachment to the pyrazine core while a second EWG may be bonded to the phenyl ring at a position ortho to the ring carbon at the point of attachment to the pyrazine core.

Typical linking moieties include (a) alkenyls (e.g., 1-propenyl, 1-butenyl, 1-hexenyl, 2,4-hexadienyl); (b) alkynyls (e.g., 1-butynyl and 2,4-hexadiynyl); (c) aryls (e.g., phenyl, naphthyl, biphenyl, and anthracene); heteroaryls (e.g., pyridine, pyrimidine, pyrazine, triazine, pyridazine, tetrazine, furan, benzofuran, thiophene, imidazole, thiazole, thiadazole, oxazole, pyrrole, indole, triazole, and nucleic acid groups such as uracil, guanine, adenine, cytosine, and thymine); (d) anilino and polyanilino, and (e) azo.

Exemplary pyrazine derivatives having an aryl π-extended system are shown below.

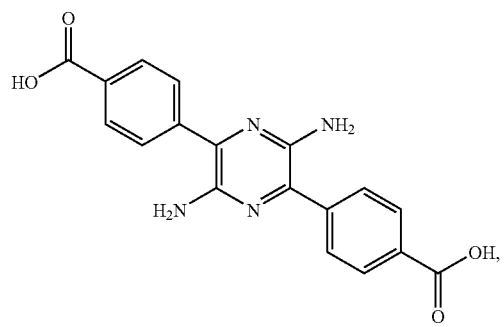

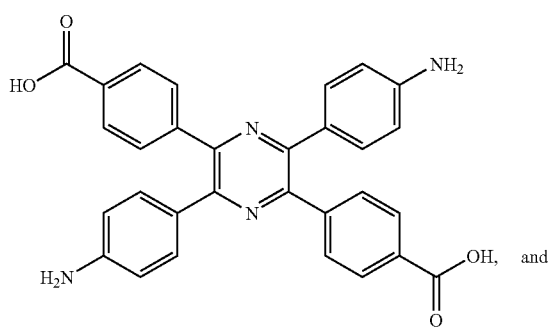

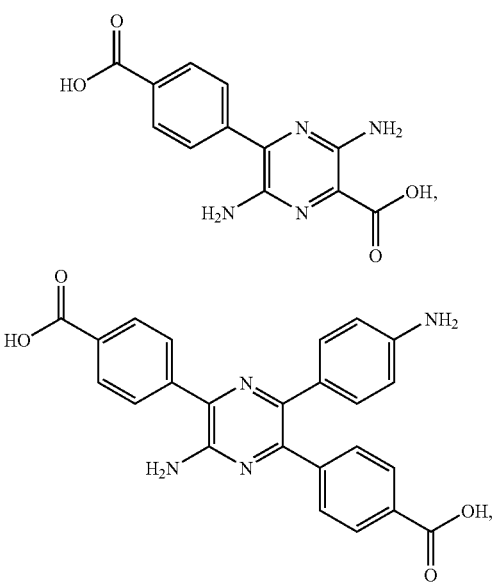

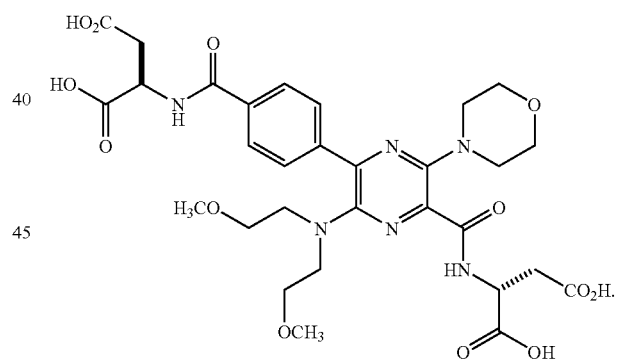

Exemplary pyrazine derivatives having a fused polycyclic aryl π-extended system are shown below.

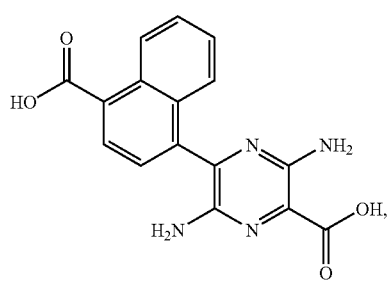

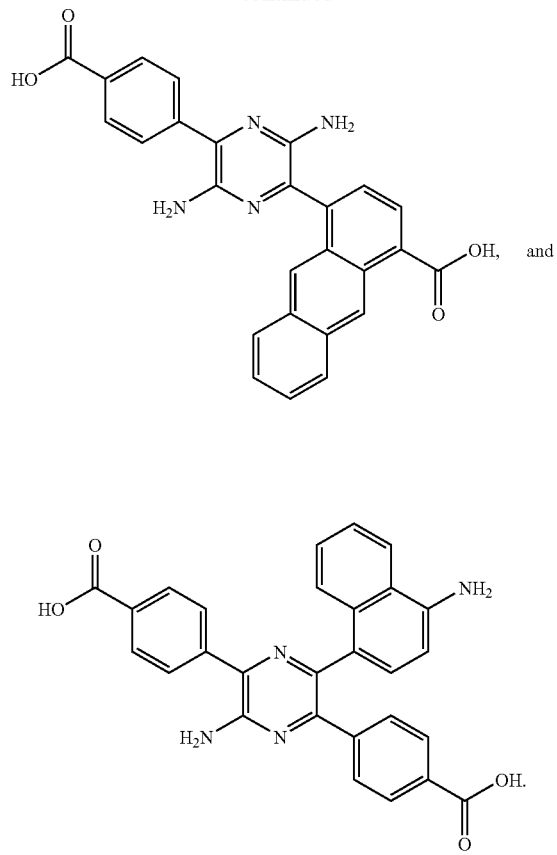
Exemplary pyrazine derivatives having a 6-membered heteroaryl π-extended system (e.g., pyridines, pyrimidines, pyrazinopyrazines, triazines, pyridazines, and tetrazines) are shown below.
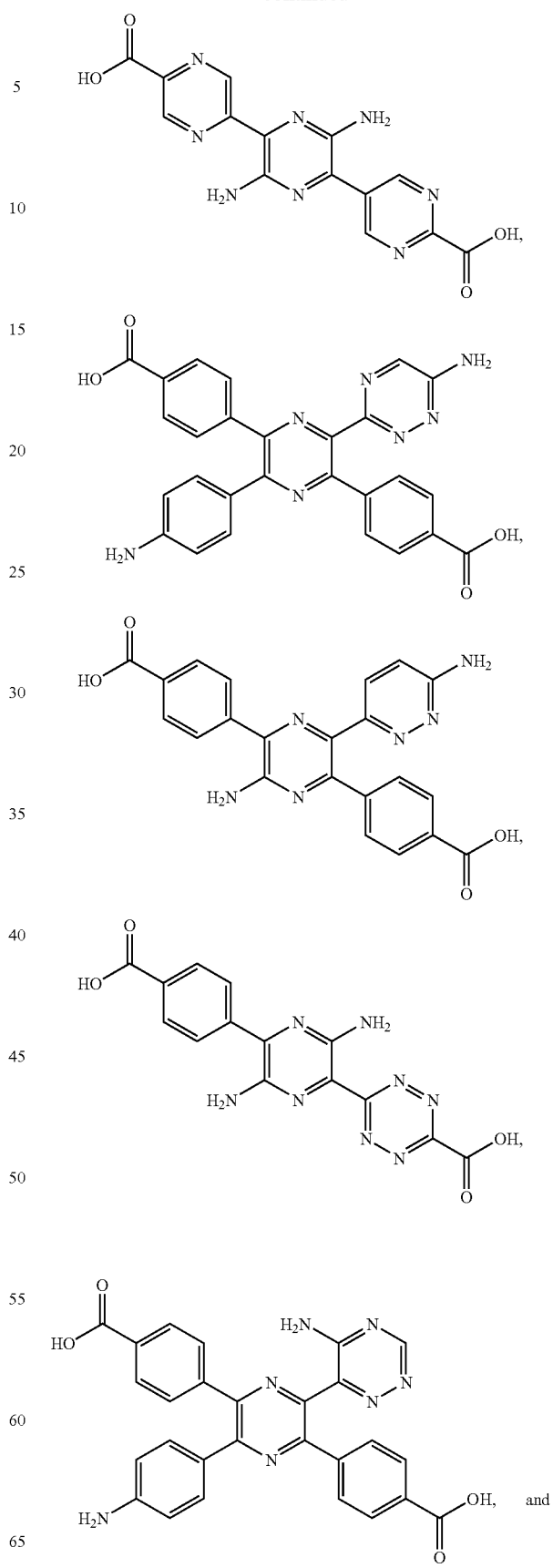

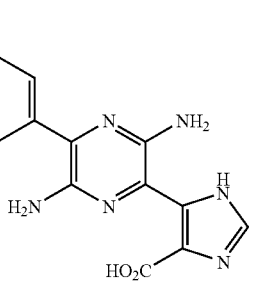
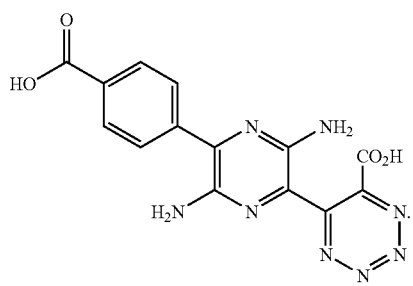
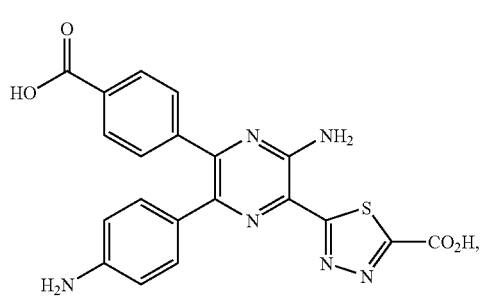
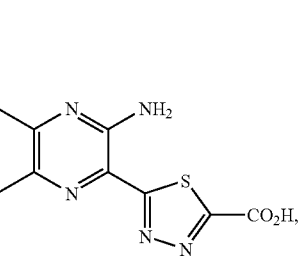
Exemplary pyrazine derivatives having a 5-membered heteroaryl π-extended system (e.g., furan, benzofuran, thiophene, imidazole, thiazole, thiadiazole, oxazole, pyrrole, indole, and triazole) are shown below.
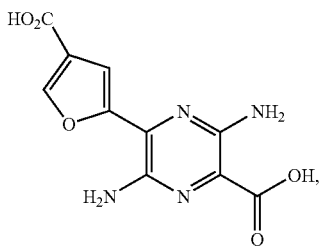
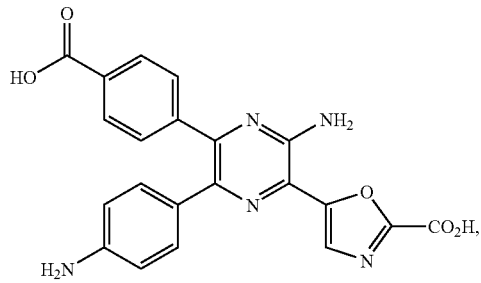
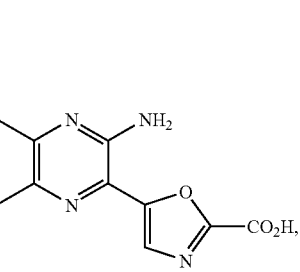
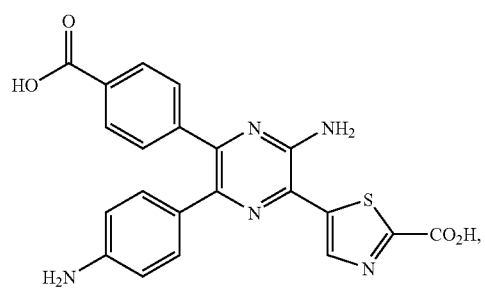
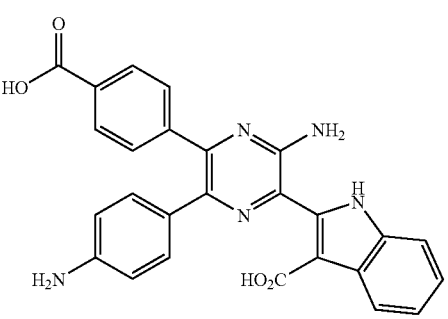
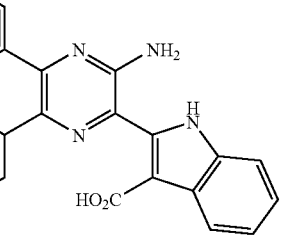
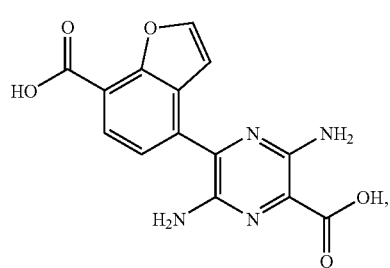
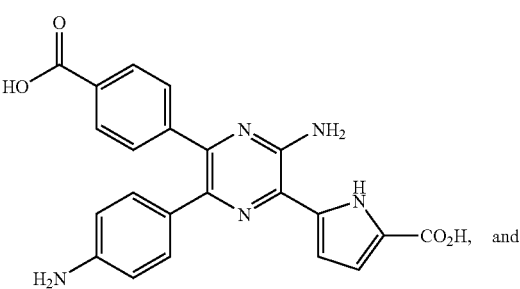
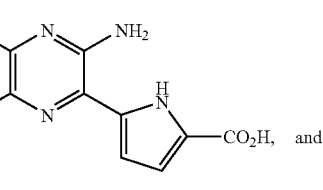
, and

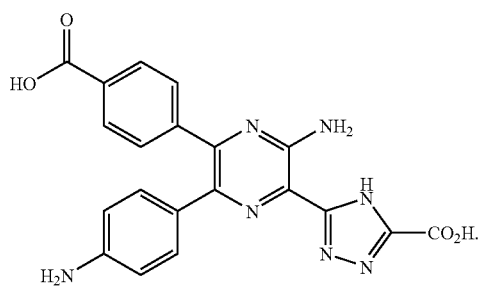
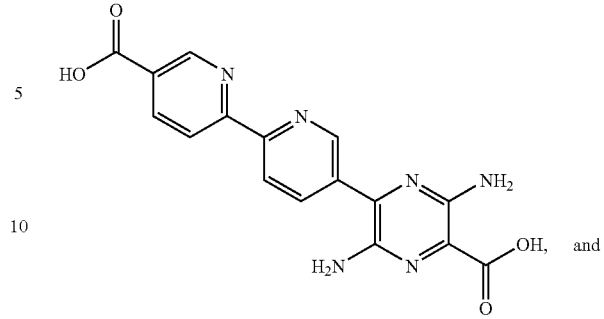
Exemplary pyrazine derivatives having a biphenyl or biheteroaryl π-extended system are shown below.
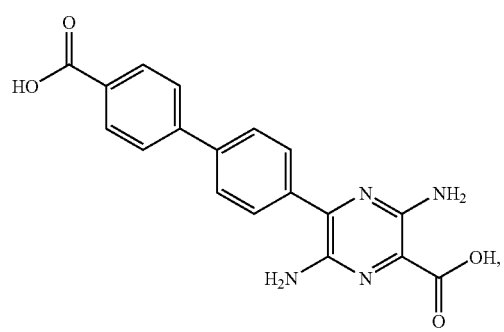
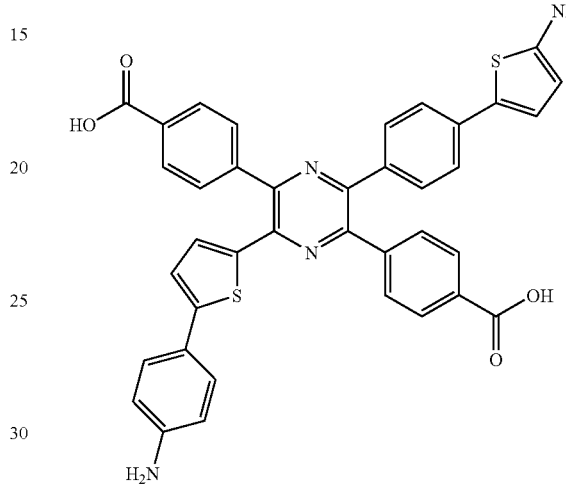
Exemplary pyrazine derivatives having a nucleic acid π-extended system (e.g., guanine, adenine, cytosine, thymine, and uracil) are shown below.
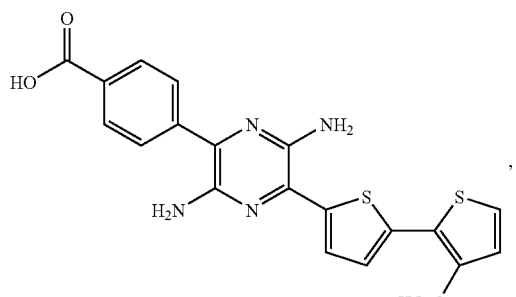
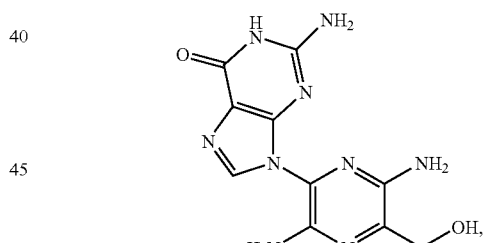
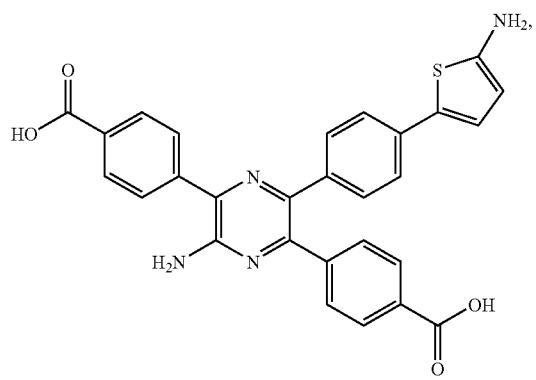
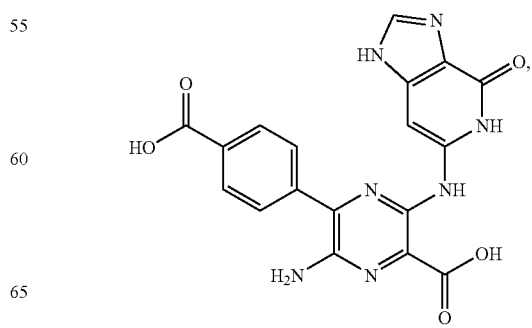

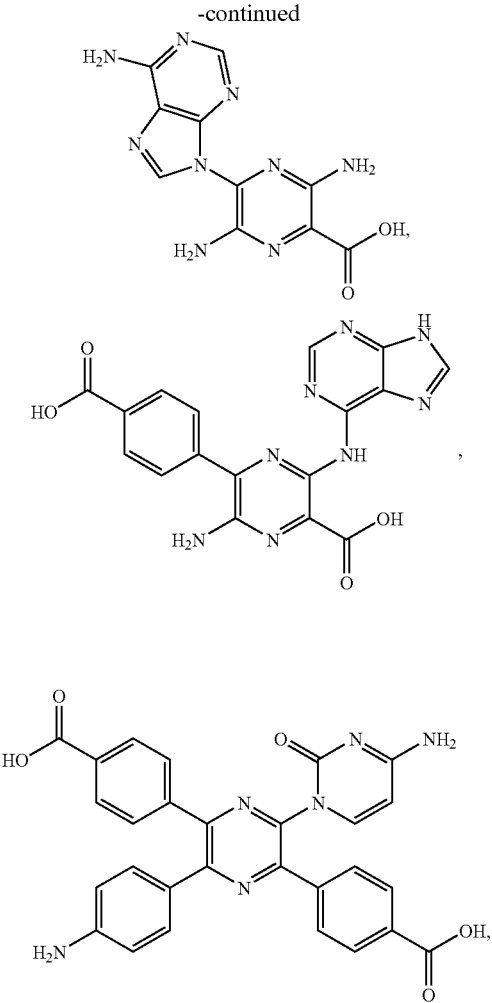
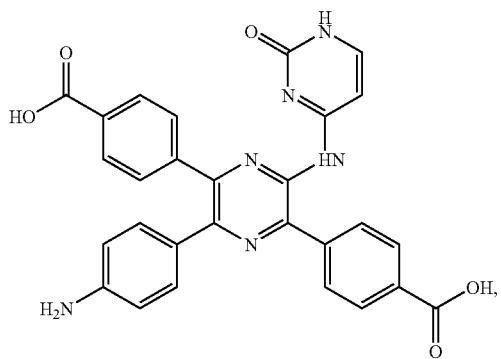
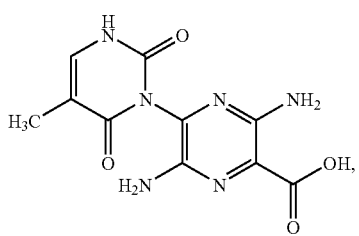
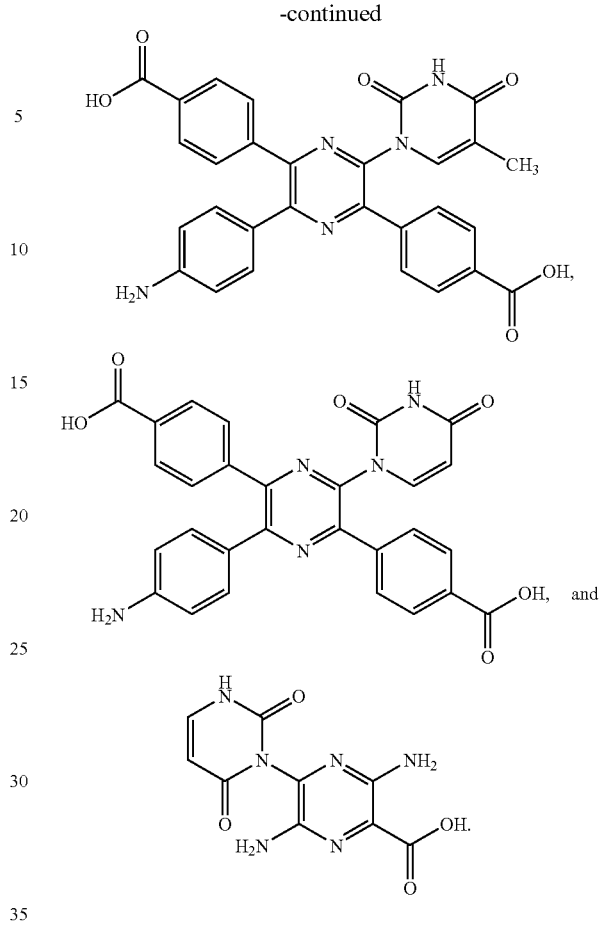
Exemplary pyrazine derivatives having an alkenyl or alkynyl nucleic acid π-extended system are shown below.
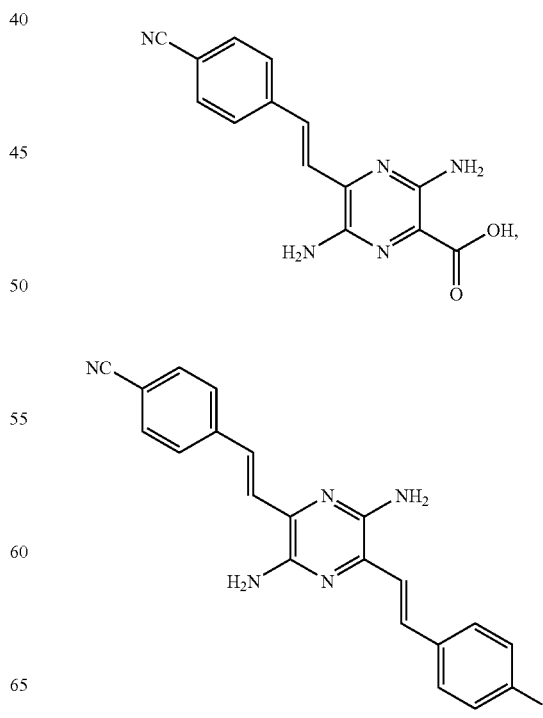

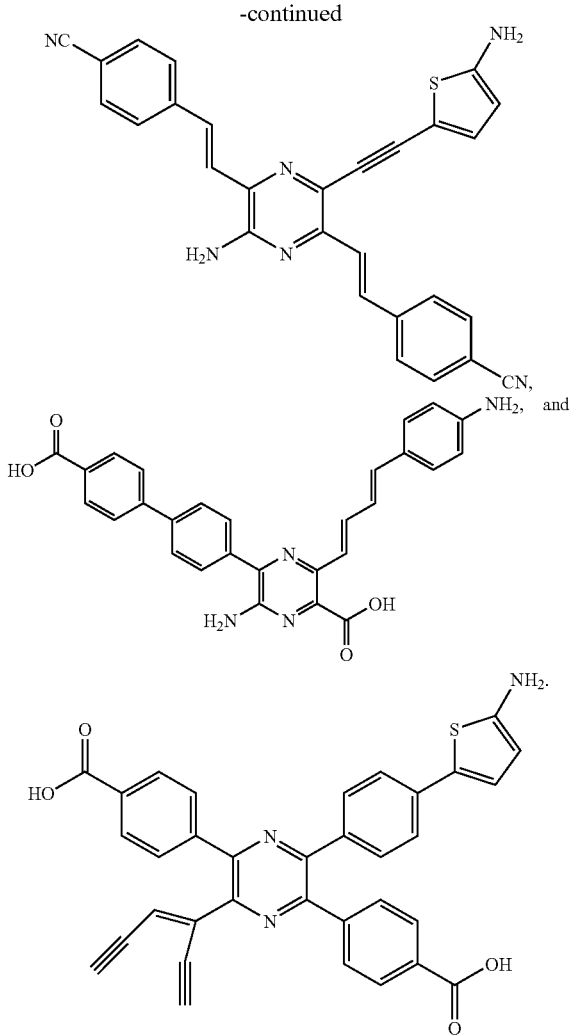

Syntheses of pyrazine derivatives, in general, have been described previously [11-13]. Preparation procedures for some of the novel pyrazine derivatives of the present invention, using procedures specifically developed for this application, are described later in Examples 1 to 11. It is noteworthy that the alkylation of the electron donating amino group in cyano- or carboxypyrazines has a profound effect on electronic transition of the pyrazine chromophore in that the dialkylation of the amino group in 2,5-diamino-3,5-dicyanopyrazine produces large bathochromic shift of about 40-60 nm. It is also noteworthy that the pyrrolidino and piperidino derivatives exhibit substantial difference in their UV spectra in that the former exhibits a bathochromic shift of about 34 nm. Thus, the pyrazine nucleus offers considerable opportunity to 'tune' the electronic properties by even simple modifications. In general, without being held to any particular theory, it is believed that conjugation (π-extension) of a chromophore or fluorophore to other unsaturated groups raises the energy level of the highest occupied molecular orbital (HOMO) and lowers the energy level of the lowest unoccupied molecular orbital (LUMO) of the molecule. As a result, less energy is required for an electronic transition in the conjugated π-system over the analogous non-conjugated pyrazine derivative. The more π-extending substituents that are attached to a pyrazine derivative, the less energy required for the electronic transition and therefore the longer the wavelength at which the transition occurs. By extending the absorption wavelengths, these pyrazine derivatives may also be used in the near infrared spectrum for imaging purposes. Furthermore, their relatively small size of pyrazines renders them ideal haptens for bioconjugate applications. However, pyrazine derivatives that absorb and emit in the red and near infrared region are required if they were to be used for molecular optical imaging and photodynamic therapy (PDT), i.e. Type II phototherapy.

The exact formulation of the pyrazine derivatives is determined based on a variety of factors including the particular use of the dye. Pyrazine derivatives of this invention can be administered as solutions in most pharmaceutically acceptable intravenous vehicles known in the art. Pharmaceutically acceptable vehicles that are well known to those skilled in the art include, but are not limited to, 0.01-0.1 M phosphate buffer or 0.8% saline. Additionally, pharmaceutically acceptable carriers may be aqueous or non-aqueous solutions, suspensions, emulsions, or appropriate combinations thereof. Examples of non-aqueous solvents are propylene glycol, polyethylene glycol, vegetable oils such as olive oil, and injectable organic esters such as ethyl oleate. Examples of aqueous carriers are water, alcoholic/aqueous solutions, emulsions or suspensions, including saline and buffered media. Exemplary parenteral vehicles include sodium chloride solution, Ringer's dextrose, dextrose and sodium chloride, lactated Ringer's or fixed oils. Exemplary intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Suitable diluents, preservatives, solubilizers, emulsifiers, adjuvant and/or carriers are also suitable excipients. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions may likely influence the physical state, solubility, stability, rate of in vivo release, and/or rate of in vivo clearance.

In accordance with the present invention, one protocol for assessing physiological function of body cells includes administering an effective amount of a pyrazine derivative represented by Formula 1, 2, or 3 into a body of a patient. An appropriate dosage of the pyrazine derivate that is administered to the patient is readily determinable by one of ordinary skill in the art and may vary according to the clinical procedure contemplated, generally ranging from about 1 nanomolar to about 100 micromolar. The administration of the pyrazine derivative to the patient may occur in any of a number of appropriate fashions including, but not limited to: (1) intravenous, intraperitoneal, or subcutaneous injection or infusion; (2) oral administration; (3) transdermal absorption through the skin; and (4) inhalation.

Still referring to the above-mentioned protocol, the pyrazine derivative is exposed to visible and/or near infrared light.

This exposure of the pyrazine derivate to light may occur at any appropriate time but preferably occurs while the pyrazine derivative is in the body (e.g., in the bloodstream) of a patient. Due to this exposure of the pyrazine derivate to the visible and/or infrared light, the pyrazine derivate emanates spectral energy (e.g., visible and/or near infrared light) that may be detected by appropriate detection equipment. The spectral energy emanated from the pyrazine derivative tends to exhibit a wavelength range greater than a wavelength range absorbed by the pyrazine derivative. For example, if an embodiment of the composition absorbs light of about 700 nm, the composition may emit light of about 745 nm.

Detection of the pyrazine derivate (or more particularly, the light emanating therefrom) may be achieved through optical fluorescence, absorbance or light scattering procedures known in the art. In one embodiment, this detection of the emanated spectral energy may be characterized as a collection of the emanated spectral energy and a generation of electrical signal indicative of the collected spectral energy. The mechanism(s) utilized to detect the spectral energy from the composition that is present in the body may be designed to detect only selected wavelengths (or wavelength ranges) and/or may include one or more appropriate spectral filters. Various catheters, endoscopes, ear clips, hand bands, head bands, surface coils, finger probes and the like may be utilized to expose the pyrazine derivatives to light and/or to detect the light emanating therefrom [14]. This detection of spectral energy may be accomplished at one or more times intermittently or may be substantially continuous.

Renal function of the patient can be determined based on the detected spectral energy. This can be achieved by using data indicative of the detected spectral energy and generating an intensity/time profile indicative of a clearance of the pyrazine derivative from the body. This profile may be correlated to a physiological or pathological condition. For example, the patient's clearance profiles and/or clearance rates may be compared to known clearance profiles and/or rates to assess the patient's renal function and to diagnose the patient's physiological condition. In the case of analyzing the presence of the pyrazine derivative in bodily fluids, concentration/time curves may be generated and analyzed (preferably in real time) using an appropriate microprocessor to diagnose renal function.

Physiological function can be assessed by: (1) comparing differences in manners in which normal and impaired cells remove a composition of the invention from the bloodstream; (2) measuring a rate or an accumulation of a composition of the invention in the organs or tissues; and/or (3) obtaining tomographic images of organs or tissues having a composition of the invention associated therewith. For example, blood pool clearance may be measured non-invasively from convenient surface capillaries such as those found in an ear lobe or a finger or can be measured invasively using an appropriate instrument such as an endovascular catheter. Accumulation of a composition of the invention within cells of interest can be assessed in a similar fashion.

A modified pulmonary artery catheter may also be utilized to, inter alia, make the desired measurements [15, 16] of spectral energy emanating from a composition of the invention. The ability for a pulmonary catheter to detect spectral energy emanating from a composition of the invention is a distinct improvement over current pulmonary artery catheters that measure only intravascular pressures, cardiac output and other derived measures of blood flow. Traditionally, critically ill patients have been managed using only the above-listed parameters, and their treatment has tended to be dependent upon intermittent blood sampling and testing for assessment of renal function. These traditional parameters provide for discontinuous data and are frequently misleading in many patient populations.

Modification of a standard pulmonary artery catheter only requires making a fiber optic sensor thereof wavelength-specific. Catheters that incorporate fiber optic technology for measuring mixed venous oxygen saturation exist currently. In one characterization, it may be said that the modified pulmonary artery catheter incorporates a wavelength-specific optical sensor into a tip of a standard pulmonary artery catheter. This wavelength-specific optical sensor can be utilized to monitor renal function-specific elimination of a designed optically detectable chemical entity such as the compositions of the present invention. Thus, by a method analogous to a dye dilution curve, real-time renal function can be monitored by the disappearance/clearance of an optically detected compound.

Formulations

Generally, compositions comprising the pyrazine derivatives of the invention may be prepared as sterile formulations, aqueous formulations, parenteral formulations and any other formulations including one or more of the pyrazine derivatives of the invention. As previously discussed, these compositions of the invention may include pharmaceutically acceptable diluents, carriers, adjuvants, preservatives, excipients, buffers, and the like. The phrase "pharmaceutically acceptable" means those formulations that are, within the scope of sound medical judgment, suitable for use in contact with the tissues of humans and animals without undue toxicity, irritation, allergic response and the like, and are commensurate with a reasonable benefit/risk ratio.

For example, for phototherapeutic or photodiagnostic uses, the pyrazine derivatives may be formulated into compositions for enteral (oral or rectal), parenteral, topical, or cutaneous administration. Topical or cutaneous delivery of the pyrazine derivative may include aerosols, creams, gels, solutions, etc. The compositions are administered in doses effective to achieve the desired or therapeutic objective. Such doses may vary widely depending upon the particular pyrazine derivative employed, the organs or tissues to be examined, the equipment employed in the clinical procedure, the efficacy of the treatment achieved, and the like. These compositions contain an effective amount of the phototherapeutic agent along with conventional pharmaceutical carriers and excipients appropriate for the type of administration contemplated. These compositions may include stabilizing agents, skin preparation enhancing agents, electrolytes such as sodium chloride, and/or pharmaceutically acceptable buffers, emulsifiers, and/or surfactants.

Formulations for enteral administration may vary widely as is well known in the art. In general, such formulations are liquids, which include an effective amount of the composition in an aqueous solution or suspension. Such enteral compositions may optionally include buffers, surfactants, emulsifiers, thixotropic agents, and the like. Compositions or oral administration may contain flavoring agents and other ingredients for enhancing their organoleptic qualities. A topical application can be formulated as a liquid solution, water/oil suspension or particles, depending on the particular nature of the agent and the type of tissue to be targeted. If the pyrazine derivative is water soluble, for instance, a solution in water may be applied to or into the target tissue. The delivery of the pyrazine derivative into and through the skin may be enhanced using well known methods and agents such as transdermal permeation enhancers.

Dosing

Generally, for all of the uses discussed above, an appropriate dosage of the pyrazine derivative administered to a patient is readily determinable by one of ordinary skill in the art and may vary according to such factors as clinical procedure contemplated, solubility, bioavailability, and toxicity. By way of example, for monitoring of renal function, an appropriate dosage typically ranges from about 1 nanomolar to about 100 micromolar.

For phototherapy, the dose of the pyrazine derivative may vary from about 0.1 mg/kg body weight to about 500 mg/kg body weight. In one embodiment, the dose is in the range of about 0.5 to about 2 mg/kg body weight. In one example, for compositions administered parenterally, a sterile aqueous solution or suspension of the pyrazine derivative may be present in a concentration ranging from about 1 nM to about 0.5 M, typically in a concentration from about 1 µM to about 10 mM.

EXAMPLES

The following examples illustrate specific embodiments of this invention. As would be apparent to skilled artisans, various changes and modifications are possible and are contemplated within the scope of the invention described.

Example 1

Synthesis of 3-(bis(2-methoxyethyl)amino)-6-chloro-5-(furan-2-yl)pyrazine-2-carbonitrile

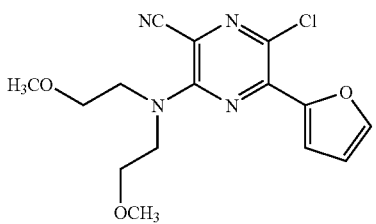

Step 1. Synthesis of 2-amino-5-bromo-3,6-dichloropyrazine. A solution of 2-amino-6-chloropyrazine (25 g, 193.1 mmol) in MeOH (500 mL) was treated with NBS (34.3 g, 193.1 mmol), portion-wise, over 1 hour. The resulting mixture was stirred for 16 hours thereafter. TLC analysis at this time shows a small amount of starting material remaining. Another 1.4 g NBS added and reaction heated to 50° C. for 2 hours. The mixture was then cooled to 38° C. and treated with NCS (25.8 g, 193.1 mmol). The reaction mixture was heated to 50° C. for 16 hours thereafter. The mixture was then cooled to room temperature and treated with water (500 mL). The precipitate was collected by filtration and dried in a vacuum dessicator to afford 45.4 g (97% yield) of 2-amino-5-bromo-3,6-dichloropyrazine as a white solid: $^{13}$C NMR (75 MHz, CDCl$_3$) δ 149.9 (s), 145.6 (s), 129.6 (s), 121.5 (s). LCMS (15-95% gradient acetonitrile in 0.1% TFA over 10 min), single peak retention time=4.51 min on 30 mm column, (M+H)$^+$=244, (M+H+ACN)$^+$=285.

Step 2. Synthesis of 5-amino-3,6-dichloropyrazine-2-carbonitrile. A mixture of CuCN (8.62 g, 96.3 mmol) and NaCN (4.72 g, 96.3 mmol) was heated under high vacuum to 90° C. The resulting mixture was subjected to three ArgonNacuum cycles and placed under a final positive pressure of Argon. The mixture was allowed to cool to room temperature and DMF (150 mL) was added. The heterogenous mixture was heated to 130° C. for 2.5 hours. To the resulting homogeneous mixture of sodium dicyanocuprate was added a solution of the product from step 1 (15.6 g, 64.2 mmol) dissolved in DMF (150 mL), dropwise, over 1 hour. The temperature was gradually raised to 150° C. and the resulting mixture was stirred at this temperature for 10 hours thereafter. The reaction was then allowed to cool to room temperature and poured into water (1 L). The resulting mixture was extracted with EtOAc (3×) and the combined extracts were filtered to remove a flocculant dark solid, washed with brine, dried (Na$_2$SO$_4$), filtered again and concentrated. Purification by flash column chromatography (SiO$_2$, 10/1 hexanes-EtOAc to 3/1) to afford 6.70 g (55% yield) of the nitrile product as a tan solid: $^{13}$C NMR (75 MHz, CDCl$_3$) δ 153.9 (s), 149.1 (s), 131.7 (s), 115.4 (s), 111.0 (s). GCMS (Ink temperature=280° C., 1.0 mL/min helium flow rate, temperature program: 100° C. (2 min hold), ramp to 300° C. @ 10° C./min (2 min hold), major peak retention time=16.556 min, m/z (EI)=188, 190.

Step 3. Synthesis of 5-amino-3-(bis(2-methoxyethyl)amino)-6-chloropyrazine-2-carbonitrile. To the product from step 2 (1.00 g, 5.29 mmol) in ACN (20 mL) was added bis(2-methoxyethyl)amine (3.0 mL, 2.71 g, 20.3 mmol) and the reaction mixture was heated to 70° C. for 16 hours thereafter. The reaction was cooled and concentrated. The residue was partitioned with EtOAc and water. The organic layer was separated and the aqueous was extracted again with EtOAc. The combined organic extracts were washed with brine, dried (Na$_2$SO$_4$), filtered and concentrated. Purification by flash column chromatography (SiO$_2$, 10/1 hexanes-EtOAc to 1/1) afforded 950 mg (63% yield) of the desired adduct as a yellow solid: $^1$NMR (300 MHz, CDCl$_3$) δ 7.47 (bs, 2 H), 3.77 (t, J=5.7 Hz, 4 H), 3.52 (t, J=5.4 Hz, 4 H), 3.25 (s, 6 H). $^{13}$C NMR (75 MHz, CDCl$_3$) δ 154.7 (s), 152.0 (s), 120.9 (s), 119.5 (s), 95.8 (s), 71.0 (t), 59.1 (q), 50.0 (t). LCMS (50-95% gradient acetonitrile in 0.1% TFA over 10 min), single peak retention time=4.91 min on 250 mm column, (M+H)$^f$=286, (M+Na)$^+$=308, (M+Na$^+$ ACN)$^+$=349.

Step 4. Synthesis of 3-(bis(2-methoxyethyl)amino)-5-bromo-6-chloropyrazine-2-carbonitrile. To the product from step 3 (1.39 g, 4.88 mmol) in 48% hydrobromic acid (20 mL) at 0° C. (ice-salt bath), was added a solution of sodium nitrite (673 mg, 9.75 mmol) in water (10 mL) dropwise over 30 min. The resulting mixture was stirred at 0-5° C. for 1 h and poured into a stirred solution of CuBr$_2$ (1.64 g, 7.34 mmol) in water (100 mL). The resulting mixture was stirred for 16 h at room temperature thereafter. The mixture was extracted with EtOAc (3×). The combined organic layers were dried (Na$_2$SO$_4$), filtered and concentrated. Purification by flash column chromatography (SiO$_2$, 50/1 CHCl$_3$-MeOH) afforded 1.00 g (58% yield) of the bromide as a orange-brown solid: $^1$NMR (300 MHz, CDCl$_3$) δ 3.99 (t, J=5.4 Hz, 4 H), 3.64 (t, J=5.4 Hz, 4 H), 3.35 (s, 6 H). $^{13}$C NMR (75 MHz, CDCl$_3$) δ 152.8 (s), 140.8 (s), 133.4 (s), 117.2 (s), 108.3 (s), 70.4 (t), 59.1 (t), 50.5 (q). LCMS (50-95% gradient acetonitrile in 0.1% TFA over 10 min), single peak retention time=4.55 min on 250 mm column, (M+H)$^+$=349, 351.

Step 5. Synthesis of 3-(bis(2-methoxyethyl)amino)-6-chloro-5-(furan-2-yl)pyrazine-2-carbonitrile. A mixture of the product from step 4 (1.0 g, 2.87 mmol), 2-furanboronic acid (643 mg, 5.75 mmol), Cs$_2$CO$_3$ (3.31 g, 10.2 mmol), TFP (35 mol %, 236 mg, 1.02 mmol), and Pd$_2$ dba$_3$-CHCl$_3$ (5 mol %, 10 mol % Pd, 150 mg) was subjected to 3 vacuum/Argon cycles and placed under a positive pressure of Argon. Anhydrous dioxane (50 mL) was added and the reaction mixture was heated to 75° C. for 16 h thereafter. The reaction mixture was cooled to room temperature, diluted with EtOAc (100 mL) and filtered through a medium frit. Concentration and purification of the residue by flash chromatography (SiO$_2$, 50/1 CHCl$_3$-MeOH) afforded the 757 mg of the furan adduct (78% yield) as a tan powder.

Example 2

2-Cyano-5-(2-furanyl)-3-[N,N-bis(2-methoxyethyl)]amino-6-(4-morpholino)pyrazine

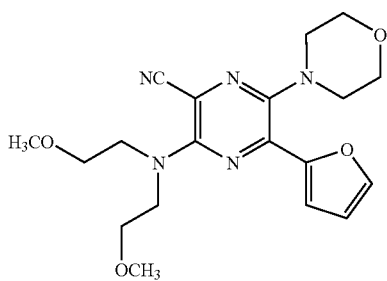

To the product from Example 1, (240 mg, 0.39 mmol) was added morpholine (5 mL). The reaction mixture was heated to 70° C. for 2 h. The mixture was cooled and concentrated. The residue was partitioned with EtOAc and water. The EtOAc layer was separated and washed with saturated sodium bicarbonate and brine. The EtOAc layer was dried (Na$_2$SO$_4$), filtered and concentrated. Purification by flash column chromatography (SiO$_2$, 3:1 to 1:1 hexanes-EtOAc) afforded 199 mg (75% yield) of the morpholine adduct as an orange foam: LCMS (15-95% gradient acetonitrile in 0.1% TFA over 10 min), single peak retention time=8.76 min on 250 mm column, (M+H)$^+$=661, (M+Na)$^+$=683.

Example 3

3,6-Bis[N,N-(2-methoxyethyl)amino]carbamoyl-N$^5$,N$^5$-bis(2-methoxyethyl)-2-(2-pyrrolo) pyrazine

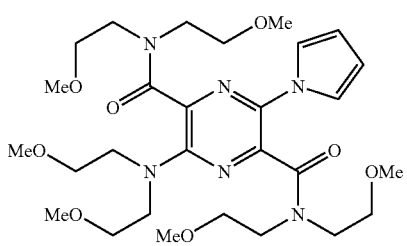 [SMILES: COCCN(CCOC)C(=O)c1nc(-n2cccc2)c(C(=O)N(CCOC)CCOC)nc1N(CCOC)CCOC]

Step 1. Synthesis of 3,6-dibromopyrazine-2,5-dicarboxylic acid. 3,6-Diaminopyrazine-2,5-dicarboxylic acid (499 mg, 2.52 mmol) was dissolved in 48% hydrobromic acid (10 mL) and cooled to 0° C. in an ice-salt bath. To this stirred mixture was added a solution of sodium nitrite (695 mg, 10.1 mmol) in water (10 mL) dropwise so that the temperature remains below 5° C. The resulting mixture was stirred for 3 h at 5-15° C., during which time the red mixture became a yellow solution. The yellow solution was poured into a solution of cupric bromide (2.23 g, 10.1 mmol) in water (100 mL) and the resulting mixture was stirred at room temperature. After an addition 3 h, the aqueous mixture was extracted with EtOAc (3×). The combined extracts were dried (Na$_2$SO$_4$), filtered and concentrated to afford 440 mg (54% yield) 3,6-dibromopyrazine-2,5-dicarboxylic acid as a pale yellow solid: $^{13}$C NMR (75 MHz, CDCl$_3$) δ 164.3 (s), 148.8 (s), 134.9 (s). HPLC (5-95% gradient acetonitrile in 0.1% TFA over 10 min), single peak retention time=2.95 min on 250 mm column.

Step 2. Synthesis of 3-(Bis(2-methoxyethyl)amino)-6-bromo-N$^2$,N$^2$,N$^5$,N$^5$-tetrakis(2-methoxyethyl)pyrazine-2,5-dicarboxamide. The product from step 1 (440 mg, 1.36 mmol) was dissolved in DMF (25 mL), treated with HOBt-H$_2$O (624 mg, 4.08 mmol), and EDC-HCl (786 mg, 4.10 mmol) and stirred for 30 min at room temperature. Bis(2-methoxy-ethyl)amine (620 mL, 559 mg, 4.20 mmol) was added and the resulting mixture was stirred at room temperature for 16 h and concentrated. The residue was partitioned with water and EtOAc. The EtOAc layer was separated and the aqueous was extracted again with EtOAc. The combined organic layers were washed with 0.5 N HCl, saturated sodium bicarbonate, and brine. The organic layer was dried (Na$_2$SO$_4$), filtered and concentrated to afford 214 mg of 3-(bis(2-methoxyethyl)amino)-6-bromo-N$^2$,N$^2$,N$^5$,N$^5$-tetrakis(2-methoxyethyl)pyrazine-2,5-dicarboxamide (26% yield) as a brown oil: LCMS (5-95% gradient acetonitrile in 0.1% TFA over 10 min), single peak retention time=3.85 min on 30 mm column, (M+H)$^+$=608.

Step 3. To the product from step 2 (10 mmol) is added pyrrole (11 mmol) and a "spatula tip" of Pd(PPh$_3$)$_4$. The resulting mixture is heated to 140° C. for 2 h. The reaction is cooled and concentrated. The residue is purified by chromatography.

Example 4

3-[Bis(2-methoxyethyl)amino]-2-cyano-6-morpholinopyrazine-5-phenylazopyrazine

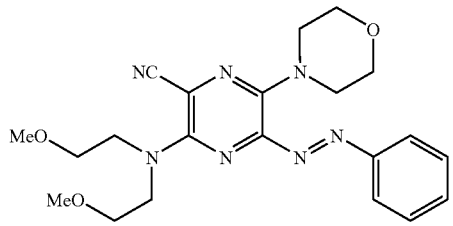

Step 1. To the product from Step 3, Example 1 (10 mmol) in ethanol (10 mL) is added nitrosobenzene (11 mmol) and about 5 drops of glacial acetic acid, and the reaction mixture is heated to 70° C. for 16 hours thereafter. The reaction is cooled and concentrated. The residue is partitioned with EtOAc and water. The organic layer is separated and the aqueous was extracted again with EtOAc. The crude product is then purified by chromatography or recrystallization.

Step 2. The azo compound is prepared by the condition similar to the one described by Taylor et al. [17]. To the product from step 1 (10 mmol) is added morpholine (5 mL). The reaction mixture is heated to 70° C. for 2 h. The mixture is cooled and concentrated. The residue is partitioned with EtOAc and water. The EtOAc layer is separated and washed with saturated sodium bicarbonate and brine. The EtOAc layer is dried (Na₂SO₄), filtered and concentrated. The crude product is the purified by chromatography or recrystallization.

Example 5

3,6-Bis(pyrrolopyrazine)-2,5-dicarboxylic acid

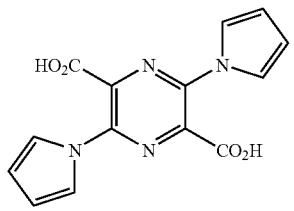 [SMILES: O=C(O)c1nc(-n2cccc2)c(C(=O)O)nc1-n1cccc1]

The condition for the preparation of the title compound is similar to the one described for pyrrolopyrazine [18]. A mixture of 3,6-Diaminopyrazine-2,5-dicarboxylic acid (10 mmol), 2,5-dimethoxytetrahydrofuran (21 mmol) in acetic acid (10 mL) is heated under reflux for 6 hours. Excess acetic acid is evaporated in vacuo and the residue is treated with water (50 mL), and the pH adjusted to about 2. The crude product is collected by filtration and purified by chromatography or recrystallization.

Example 6

(R)-2-(6-(bis(2-methoxyethyl)amino)-5-(4-carboxyphenyl)-3-morpholinopyrazine-2-carboxamido) succinic acid

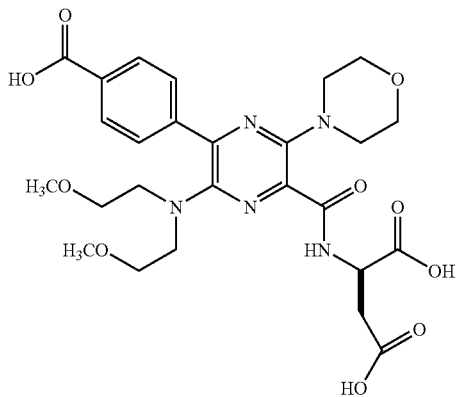 [SMILES: COCCN(CCOC)c1nc(C(=O)N[C@H](CC(=O)O)C(=O)O)c(N2CCOCC2)nc1-c1ccc(C(=O)O)cc1]

Step 1. To the product from Example 1, Step 1,2-amino-5-bromo-3,6-dichloropyrazine (1.00 g, 4.15 mmol) was added 4-(benzyloxycarbonyl)phenylboronic acid (1.59 g, 6.53 mmol), Pd₂ dba₃.CHCl₃(2.5 mol %, 5 mol %, 106 mg, 0.10 mmol), tris(2-furyl)phosphine (8 mol %, 76.2 mg, 0.33 mmol) and Cs₂CO₃ (3 equiv., 4.0 g, 12.3 mmol). The resulting mixture was subjected to three vacuum/Argon cycles and placed under a final Argon flow atmosphere. Dioxane (50 mL) was added via syring and the reaction was then heated to 75° C. for 16 h. The reaction was cooled and filtered through a medium frit. Concentration and purification by flash chromatography (SiO₂, 3/1 hexanes/EtOAc) afforded the desired product.

Step 2. The product from step 1 (1 mmol) is dissolved in ACN (20 mL) and treated with bis(2-methoxy)ethylamine (5 mmol). The resulting mixture is heated to 75° C. for 16 h. Concentration affords the desired product, benzyl 4-{5-amino-3-[bis(2-methoxyethyl)amino]-6-chloropyrazin-2-yl} benzoate.

Step 3. The product from step 2 (1 mmol) is dissolved in ACN (50 mL) and treated with CuBr₂ (3 mmol). The resulting stirred mixture is treated with Cert-butyl nitrite (1.5 mmol) drop-wise over 15 min. The resulting mixture is stirred for 2 h at room temperature and poured into a saturated ammonium chloride solution (100 mL). The resulting mixture is extracted with ethyl acetate (3×). The combined extracts are dried (Na₂SO₄), filtered and concentrated to afford the desired product, benzyl 4-(3-(bis(2-methoxyethyl)amino)-5-bromo-6-chloropyrazin-2-yl)benzoate.

Step 4. To the product from step 3 (1 mmol) is added 2-furanboronic acid (1.5 mmol), Pd₂ dba₃-CHCl₃(2.5 mol %), tris(2-furyl)phosphine (8 mol %) and Cs₂CO₃ (3 mmol). The resulting mixture is subjected to three vacuum/Argon cycles and placed under a final Argon flow atmosphere. Dioxane (30 mL) is added via syring and the reaction is then heated to 75° C. for 16 h. The reaction is cooled and filtered through a medium frit. Concentration and purification by flash chromatography affords the desired product, benzyl 4-(3-(bis(2-methoxyethyl)amino)-6-chloro-5-(furan-2-yl)pyrazin-2-yl) benzoate.

Step 5. To a well stirred mixture of ACN (11 mL), CCl₄ (7 mL) and water (11 mL) are added sodium periodate (5 mmol) and ruthenium(IV) oxide hydrate (0.1 mmol). This mixture is stirred vigorously at room temperature for 30 minutes and treated with sodium bicarbonate (25 mmol) and water (5 mL). After 15 additional minutes, the product from step 4 (1 mmol) in ACN (1 mL) is added and the reaction is stirred for 3 h at room temperature. The mixture is poured into a separatory funnel and diluted with brine. The mixture is extracted with ethyl acetate. The layers are separated and the pH of the aqueous layer is adjusted to 3-4 with 0.5N HCl. The resulting aqueous solution is extracted with ethyl acetate (2×). The combined extracts are dried (Na₂SO₄), filtered and concentrated to afford the desired product, 5-(4-(benzyloxycarbonyl)phenyl)-6-(bis(2-methoxyethyl)amino)-3-chloropyrazine-2-carboxylic acid.

Step 6. To the product from step 5 (1 mmol) is added EDC.HCl (1.5 mmol), HOBt.H₂O (1.5 mmol) and DMF (25 mL) and the resulting mixture is stirred for 30 min. To this mixture is added H-D-Asp(OBzl)-OBzl-p-tosylate (1.5 mmol) and TEA (2 mL). The reaction is stirred for 16 h. The mixture is concentrated and the residue is partitioned with water and ethyl acetate. The ethyl acetate layer is washed with saturated sodium bicarbonate and brine. The ethyl acetate solution is dried, filtered and concentrated to afford the desired product, (R)-dibenzyl 2-(5-(4-(benzyloxycarbonyl) phenyl)-6-(bis(2-methoxyethyl)amino)-3-chloropyrazine-2-carboxamido)succinate.

Step 7. To the product from step 6 (1 mmol) is added morpholine (5 mL). The resulting mixture is heated to 70° C. for 2 h. Concentration affords the desired product, (R)-dibenzyl 2-(5-(4-(benzyloxycarbonyl)phenyl)-6-(bis(2-methoxyethyl)amino)-3-morpholinopyrazine-2-carboxamido)succinate.

Step 8. To the product from step 7 (1 mmol) in methanol (20 mL) and water (10 mL) is added 10% Pd on carbon (200 mg). To this mixture is added ammonium formate (400 mg) and the reaction is heated to reflux for 1 h. The mixture is cooled and filtered through a plug of celite with the aide of additional methanol. Concentration affords the desired product, Example 6, (R)-2-(6-(bis(2-methoxyethyl)amino)-5-(4-carboxyphenyl)-3-morpholinopyrazine-2-carboxamido)succinic acid.

Example 7

4'-(3,6-bis(bis(2-methoxyethyl)amino)-5-(4-carboxyphenyl)pyrazin-2-yl)biphenyl-4-carboxylic acid

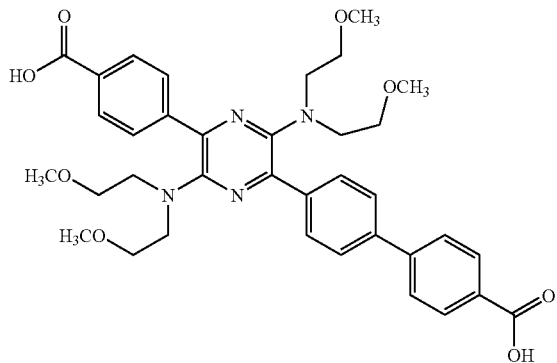 [SMILES: COCCN(CCOC)c1nc(-c2ccc(-c3ccc(C(=O)O)cc3)cc2)c(N(CCOC)CCOC)nc1-c1ccc(C(=O)O)cc1]

Step 1. To the product from Example 6, step 3 (1 mmol) is added 4'-(benzyloxycarbonyl)biphenyl-4-ylboronic acid (1.5 mmol), Pd$_2$ dba$_3$-CHCl$_3$ (2.5 mol %), tris(2-furyl)phosphine (8 mol %) and Cs$_2$CO$_3$ (3 mmol). The resulting mixture is subjected to three vacuum/Argon cycles and placed under a final Argon flow atmosphere. Dioxane (30 mL) is added via syring and the reaction is then heated to 75° C. for 16 h. The reaction is cooled and filtered through a medium frit. Concentration and purification by flash chromatography affords the desired product, benzyl 4'-(5-(4-(benzyloxycarbonyl)phenyl)-6-(bis(2-methoxyethyl)amino)-3-chloropyrazin-2-yl)biphenyl-4-carboxylate.

Step 2. To the product from step 1 (1 mmol) is added bis(2-methoxy)ethylamine (5 mL) and the mixture is heated to 100° C. for 12 h. The mixture is then concentrated to afford the desired product, benzyl 4'-(5-(4-(benzyloxycarbonyl)phenyl)-3,6-bis(bis(2-methoxyethyl)amino)pyrazin-2-yl)biphenyl-4-carboxylate.

Step 3. To the product from step 2 (1 mmol) in methanol (20 mL) and water (10 mL) is added 10% Pd on carbon (200 mg). To this mixture is added ammonium formate (400 mg) and the reaction is heated to reflux for 1 h. The mixture is cooled and filtered through a plug of celite with the aide of additional methanol. Concentration affords the desired product, Example 7, 4'-(3,6-bis(bis(2-methoxyethyl)amino)-5-(4-carboxyphenyl)pyrazin-2-yl)biphenyl-4-carboxylic acid.

Example 8

5-(3,6-bis(bis(2-methoxyethyl)amino)-5-(4-carboxyphenyl)pyrazin-2-yl)picolinic acid

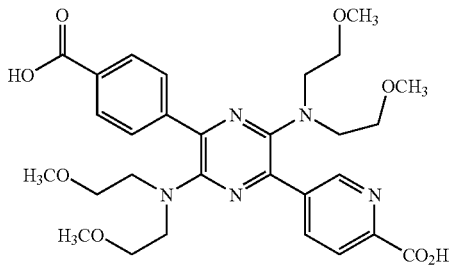 [SMILES: COCCN(CCOC)c1nc(-c2ccc(C(=O)O)nc2)c(N(CCOC)CCOC)nc1-c1ccc(C(=O)O)cc1]

Step 1. To the product from Example 6, step 3 (1 mmol) is added 6-(benzyloxycarbonyl)pyridin-3-ylboronic acid (1.5 mmol), Pd$_2$ dba$_3$-CHCl$_3$ (2.5 mol %), tris(2-furyl)phosphine (8 mol %) and Cs$_2$CO$_3$ (3 mmol). The resulting mixture is subjected to three vacuum/Argon cycles and placed under a final Argon flow atmosphere. Dioxane (30 mL) is added via syring and the reaction is then heated to 75° C. for 16 h. The reaction is cooled and filtered through a medium frit. Concentration and purification by flash chromatography affords the desired product, benzyl 5-(5-(4-(benzyloxycarbonyl)phenyl)-6-(bis(2-methoxyethyl)amino)-3-chloropyrazin-2-yl)picolinate.

Step 2. To the product from step 1 (1 mmol) is added bis(2-methoxy)ethylamine (5 mL) and the mixture is heated to 100° C. for 12 h. The mixture is then concentrated to afford the desired product.

Step 3. To the product from step 2 (1 mmol) in methanol (20 mL) and water (10 mL) is added 10% Pd on carbon (200 mg). To this mixture is added ammonium formate (400 mg) and the reaction is heated to reflux for 1 h. The mixture is cooled and filtered through a plug of celite with the aide of additional methanol. Concentration affords the desired product, Example 8,5-(3,6-bis(bis(2-methoxyethyl)amino)-5-(4-carboxyphenyl)pyrazin-2-yl)picolinic acid.

Example 9

(E)-4-(2-(3,6-bis(bis(2-methoxyethyl)amino)-5-(4-carboxyphenyl)pyrazin-2-yl)vinyl)benzoic acid

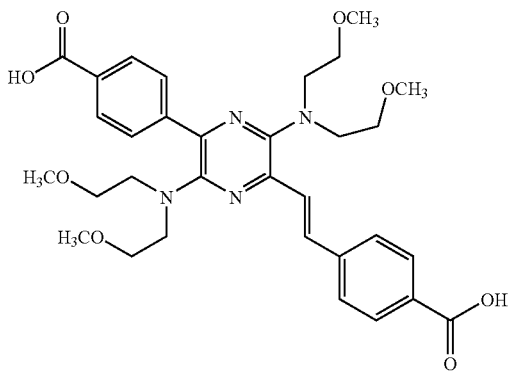 [SMILES: COCCN(CCOC)c1nc(-c2ccc(C(=O)O)cc2)c(N(CCOC)CCOC)nc1/C=C/c1ccc(C(=O)O)cc1]

Step 1. To the product from Example 6, step 3 (1 mmol) is added 6-(E)-4-(methoxycarbonyl)styrylboronic acid (1.5 mmol), Pd$_2$ dba$_3$.CHCl$_3$ (2.5 mol %), tris(2-furyl)phosphine (8 mol %) and Cs$_2$CO$_3$ (3 mmol). The resulting mixture is subjected to three vacuum/Argon cycles and placed under a final Argon flow atmosphere. Dioxane (30 mL) is added via syring and the reaction is then heated to 75° C. for 16 h. The reaction is cooled and filtered through a medium frit. Concentration and purification by flash chromatography affords the desired product, (E)-benzyl 4-(3-(bis(2-methoxyethyl)amino)-6-chloro-5-(4-(methoxycarbonyl)styryl)pyrazin-2-yl)benzoate.

Step 2. To the product from step 1 (1 mmol) is added bis(2-methoxy)ethylamine (5 mL) and the mixture is heated to 100° C. for 12 h. The mixture is then concentrated to afford the desired product, (E)-benzyl 4-(3,6-bis(bis(2-methoxyethyl)amino)-5-(4-(methoxycarbonyl)styryl)pyrazin-2-yl)benzoate.

Step 3. To the product from step 2 (1 mmol) in THF (20 mL) is added 1N NaOH (20 mL). The mixture is stirred at room temperature for 6 h. The pH is adjusted to ~3 with 1N HCl and the mixture is extracted with ethyl acetate (3×). The combined extracts are dried (Na$_2$SO$_4$), filtered and concentrated to afford the desired product, Example 9, (E)-4-(2-(3,6-bis(bis(2-methoxyethyl)amino)-5-(4-carboxyphenyl)pyrazin-2-yl)vinyl)benzoic acid.

Example 10

4-(3,6-bis(bis(2-methoxyethyl)amino)-5-(carboxyethynyl)pyrazin-2-yl)benzoic acid

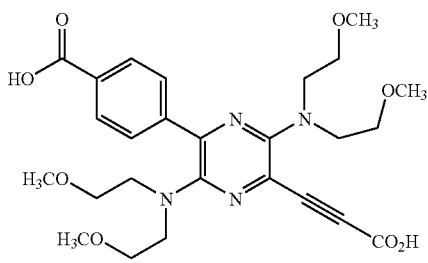 [SMILES: COCCN(CCOC)c1nc(-c2ccc(C(=O)O)cc2)c(N(CCOC)CCOC)nc1C#CC(=O)O]

Step 1. To the product from Example 6, step 3 (1 mmol) is added methyl propiolate (1.5 mmol), $PdCl_2(PCy_3)_2$ (3-10 mol %) and $Cs_2CO_3$ (3 mmol). The resulting mixture is subjected to three vacuum/Argon cycles and placed under a final Argon flow atmosphere. DMSO (30 mL) is added via syring and the reaction is then heated to 100-110° C. for 16 h. The reaction is cooled and filtered through a medium frit. Concentration and purification by flash chromatography affords the desired product, benzyl 4-(3-(bis(2-methoxyethyl)amino)-6-chloro-5-(3-methoxy-3-oxoprop-1-ynyl)pyrazin-2-yl)benzoate.

Step 2. To the product from step 1 (1 mmol) is added bis(2-methoxy)ethylamine (5 mL) and the mixture is heated to 100° C. for 12 h. The mixture is then concentrated to afford the desired product, benzyl 4-(3,6-bis(bis(2-methoxyethyl) amino)-5-(3-methoxy-3-oxoprop-1-ynyl)pyrazin-2-yl)benzoate.

Step 3. To the product from step 2 (1 mmol) in THF (20 mL) is added 1N NaOH (20 mL). The mixture is stirred at room temperature for 6 h. The pH is adjusted to –3 with 1N HCl and the mixture is extracted with ethyl acetate (3×). The combined extracts are dried ($Na_2SO_4$), filtered and concentrated to afford the desired product, Example 10, 4-(3,6-bis (bis(2-methoxyethyl)amino)-5-(carboxyethynyl)pyrazin-2-yl)benzoic acid.

Example 11

4,4'-(3,6-bis(4-(bis(2-methoxyethyl)amino)phenyl) pyrazine-2,5-diyl)dibenzoic acid

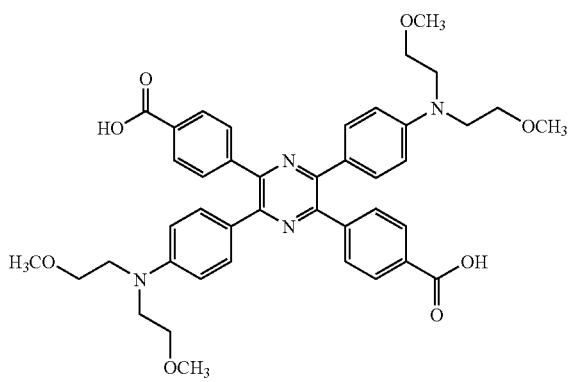 [SMILES: COCCN(CCOC)c1ccc(-c2nc(-c3ccc(C(=O)O)cc3)c(-c3ccc(N(CCOC)CCOC)cc3)nc2-c2ccc(C(=O)O)cc2)cc1]

Step 1. The product from Example 6, step 1 (1 mmol) was dissolved in ACN (25 mL) and treated with $CuBr_2$ (1.5 mmol). To this stirred mixture was added tert-butyl nitrite (1.5 mmol) drop-wise over 15 min. The resulting mixture was stirred at room temperature for 16 and poured into a saturated ammonium chloride solution (100 mL). The resulting mixture is extracted with ethyl acetate (3×). The combined extracts are dried ($Na_2SO_4$), filtered and concentrated to afford the desired product, benzyl 4-(5-bromo-3,6-dichloro-pyrazin-2-yl)benzoate.

Step 2. To the product step 1 (1 mmol) is added 4-(benzy-loxycarbonyl)phenylboronic acid (1.59 g, 6.53 mmol), $Pd_2 dba_3 \cdot CHCl_3$ (2.5 mol %, 5 mol %, 106 mg, 0.10 mmol), tris (2-furyl)phosphine (8 mol %, 76.2 mg, 0.33 mmol) and $Cs_2CO_3$ (3 equiv., 4.0 g, 12.3 mmol). The resulting mixture is subjected to three vacuum/Argon cycles and placed under a final Argon flow atmosphere. Dioxane (50 mL) is added via syring and the reaction is then heated to 75° C. for 16 h. The reaction is cooled and filtered through a medium frit. Concentration and purification by flash chromatography ($SiO_2$, 3/1 hexanes/EtOAc) affords the desired product, benzyl 4,4'-(3,6-dichloropyrazine-2,5-diyl)dibenzoate.

Step 3. To the product from step 2 (1 mmol) is added 4-(bis(2-methoxyethyl)amino)-phenylboronic acid (3.0 mmol), $PdCl_2(PCY_3)_2$ (3-10 mol %) and $Cs_2CO_3$ (6 mmol). The resulting mixture is subjected to three vacuum/Argon cycles and placed under a final Argon flow atmosphere. Dioxane (30 mL) is added via syring and the reaction is then heated to 100° C. for 16 h. The reaction is cooled and filtered through a medium frit. Concentration and purification by flash chromatography affords the desired product, benzyl 4,4'-(3,6-bis (4-(bis(2-methoxyethyl)amino)phenyl)pyrazine-2,5-diyl) dibenzoate.

Step 4. To the product from step 2 (1 mmol) in methanol (20 mL) and water (10 mL) is added 10% Pd on carbon (200 mg). To this mixture is added ammonium formate (400 mg) and the reaction is heated to reflux for 1 h. The mixture is cooled and filtered through a plug of celite with the aide of additional methanol. Concentration affords the desired product, Example 11, 4,4'-(3,6-bis(4-(bis(2-methoxyethyl)amino) phenyl)pyrazine-2,5-diyl)dibenzoic acid.

References

1. Hassan, M.; Klaunberg, B. A. Biomedical applications of fluorescence imaging in vivo. *Comparative Medicine* 2004, 54(6), 635-644.
2. Licha, K.; Olbrich, C. Optical imaging in drug discovery and diagnostic applications. *Advances in Drug Delivery Reviews* 2005, 57(8), 1087-1108.
3. Shah, K.; Weissleder, R. Molecular optical imaging: applications leading to the development of present day therapeutics. *NeuroRx* 2005, 2(2), 215-225.
4. Solban N.; Ortel, B.; Pogue, B.; Hasan, T. Targeted optical imaging and photodynamic therapy. *Ernst Schering Research Foundation Workshop* 2005, 49, 229-258.
5. Jain, R. K. Barriers to Drug Delivery in Solid Tumors. *Scientific American* 1994, 271, 58-65.
6. Sekar, N. Pyrazine dyes: An update. *Colourage* 1999, 41-44.
7. Shirai, K. et al. Synthesis and fluorescent properties of 2,5-diamino-3,6-dicyanopyrazine dyes. *Dyes and Pigments* 1998, 39.49-68.
8. Kim, J. H. et al. Self-assembling of aminopyrazine fluorescent dyes and their solid state spectra. *Dyes and Pigments* 1998, 39, 341-357.
9. M. Blanchard-Desce, M. Barzoukas *J. Chem. Phys.* 2000, 113, 3951.

10. S. Kershaw, Two-Photon Absorption. In *Characterizations, Techniques, and Tabulations for Organic Non-Linear Optical Materials*, Chapter 7, pp 515-654.
11. Bailin, G. B. The pyrazines. In The Chemistry of Heterocyclic Compounds. A. Weissberger and E. C. Taylor, Eds. John Wiley & Sons, New York: 1982.
12. Donald, D. S. Synthesis of 3,5-diaminopyrazinoic acid from 3,5-diamino-2,6-dicyanopyrazine and intermediates. U.S. Pat. No. 1976; 3,948,895.
13. Donald, D. S. Diaminosubstituted dicyanopyrzines and process. U.S. Pat. No. 1974; 3,814,757.
14. Muller et al. Eds, *Medical Optical Tomography, SPIE* Volume IS11, 1993.
15. R. B. Dorshow et al. Non-Invasive Fluorescence Detection of Hepatic and Renal Function, *Bull. Am. Phys. Soc.* 1997, 42, 681.
16. R. B. Dorshow et al. Monitoring Physiological Function by Detection of Exogenous Fluorescent Contrast Agents. In *Optical Diagnostics of Biological Fluids IV*, A. Priezzhev and T. Asakura, Editors, Proceedings of SPIE 1999, 3599, 2-8).
17. Taylor, E. C. et al. *J. Org. Chem.* 1982, 47, 552.
18. Laduree, D. et al. *Heterocycles* 1984, 22(2), 299-301.

What is claimed is:

1. A method of optically diagnosing renal function in a patient, comprising the steps of:
   administering a pyrazine derivative or a pharmaceutically-acceptable salt thereof to a patient;
   exposing the administered pyrazine derivative to visible and/or near infrared light;
   detecting spectral energy emanating from the administered pyrazine derivative; and
   determining clearance of the pyrazine derivative from the body of the patient;
   wherein the administered pyrazine derivative absorbs and emanates spectral energy in the visible and/or near infrared spectrum;
   wherein the pyrazine derivative is of the following Formula 1, and wherein:

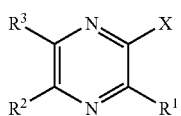

Formula 1

X is —Ar—Y, —C($R^4$)=C($R^5$)—Ar—Y, —C≡C—Ar—Y, —N=N—Ar—Y, —CO—Ar—Y, —N($R^6$)—Ar—Y, —O—Ar—Y, —S—Ar—Y, —SO—Ar—Y, —$SO_2$—Ar—Y, —C($R^4$)=C($R^5$)—Y, or —C≡C—Y;

Ar is phenyl, biphenyl, pyridyl, pyridazyl, pyrimidinyl, pyrazinyl, pyrrolyl, furanyl, thiopheneyl, pyrazolyl, imidazolyl, oxazolyl, thiazolyl, triazinyl, triazolyl or thiadiazolyl; with the proviso that if Ar is phenyl, pyrrolyl, or thiopheneyl, then at least one of $R^1$, $R^2$, and $R^3$ is other than hydrogen;

each Y is independently hydrogen, $C_1$-$C_{10}$ alkyl, halo, trihaloalkyl, —CN, —$CO_2R^7$, —$CONR^8R^9$, —$COR^{10}$, —$NO_2$, —$SOR^{11}$, —$SO_2R^{12}$, —$SO_2OR^{13}$, —$PO_3R^{14}R^{15}$, —$OR^{16}$, —$SR^{17}$, —$NR^{18}R^{19}$, —$N(R^{20})COR^{21}$, —$P(R^{22})_3$, —CO(AA)$_j$, or —CONH(PS)$_k$;

each of, $R^1$, $R^2$ and $R^3$ is independently hydrogen, $C_1$-$C_{10}$ alkyl, halo, trihaloalkyl, —CN, —$CO_2R^7$, —$CONR^8R^9$, —$COR^{10}$, —$NO_2$, —$SOR^{11}$, —$SO_2R^{12}$, —$SO_2OR^{13}$, —$PO_3R^{14}R^{15}$, —$OR^{16}$, —$SR^{17}$, —$NR^{18}R^{19}$, —$N(R^{20})COR^{21}$, —$P(R^{22})_3$, —CO(AA)$_j$, —CONH(PS)$_k$, or X;

(AA)$_j$ is a polypeptide chain comprising the same or different natural or unnatural α-amino acids linked together by peptide bonds, wherein j is an integer from 1 to 50;

(PS)$_k$ is a sulfated or non-sulfated polysaccharide chain comprising the same or different monosaccharide units connected together by glycosidic linkages, wherein k is an integer from 1 to 50;

each of $R^4$ to $R^{22}$ is independently —H, $C_1$-$C_{10}$ alkyl, —(CH$_2$)$_a$OR$^{23}$, —CH$_2$(CHOH)$_a$R$^{24}$, —CH$_2$(CHOH)$_a$CO$_2$H, —(CHCO$_2$H)$_a$CO$_2$H, —(CH$_2$)$_a$NR$^{25}$R$^{26}$, —CH[(CH$_2$)$_b$NH$_2$]$_a$CO$_2$H, —CH[(CH$_2$)$_b$NH$_2$]$_a$CH$_2$OH, —CH$_2$(CHNH$_2$)$_a$CH$_2$NR$^{27}$R$^{28}$, —(CH$_2$CH$_2$O)$_c$R$^{29}$, or —(CH$_2$)$_d$CO(CH$_2$CH$_2$O)$_c$R$^{30}$;

each of $R^{23}$ to $R^{30}$ is independently —H or —$CH_3$;

each of a, b, and d is independently an integer from 1 to 10; and c is an integer from 1 to 100.

2. The method of claim 1 wherein X is —Ar—Y, —C($R^4$)=C($R^5$)—Ar—Y, —C≡C—Ar—Y, —N=N—Ar—Y, —CO—Ar—Y, —N($R^6$)—Ar—Y, —O—Ar—Y, —S—Ar—Y, —SO—Ar—Y, or —$SO_2$—Ar—Y.

3. The method of claim 1 wherein X is —Ar—Y.

4. The method of claim 1 wherein X is —C($R^4$)=C($R^5$)—Ar—Y.

5. The method of claim 1 wherein X is —N=N—Ar—Y.

6. The method of claim 1 wherein Ar is phenyl, biphenyl, pyridyl, pyrazinyl, pyrrolyl, furanyl, and thiopheneyl.

7. The method of claim 1 wherein Ar is phenyl, pyridyl, pyrazinyl, pyrrolyl, furanyl, or thiopheneyl.

8. The method of claim 1 wherein Ar is phenyl, pyrrolyl, or furanyl.

9. The method of claim 1 wherein Ar is phenyl.

10. The method of claim 1 wherein Ar is pyrrolyl.

11. The method of claim 1 wherein Ar is furanyl.

12. The method of claim 1 wherein Y is —H, $C_1$-$C_{10}$ alkyl, halo, trihaloalkyl, —CN, —$CO_2R^7$, —$CONR^8R^9$, —$COR^{10}$, —$NO_2$, —$SO_2R^{12}$, —$OR^{16}$, —$SR^{17}$, —$NR^{18}R^{19}$, —$N(R^{20})COR^{21}$, —CO(AA)$_j$, or —CONH(PS)$_k$.

13. The method of claim 1 wherein Y is —H, $C_1$-$C_{10}$ alkyl, halo, trihaloalkyl, —CN, —$CO_2R^7$, —$CONR^8R^9$, —$OR^{16}$, —$NR^{18}R^{19}$, or —$N(R^{20})COR^{21}$.

14. The method of claim 1 wherein Y is —H, —CN, —$CO_2R^7$, —$CONR^8R^9$, —$OR^{16}$, —$NR^{18}R^{19}$, or —$N(R^{20})COR^{21}$.

15. The method of claim 1 wherein Y is —H, —$CO_2R^7$, —$OR^{16}$, or —$NR^{18}R^{19}$.

16. The method of claim 1 wherein Y is —H.

17. The method of claim 1 wherein each of $R^1$ to $R^3$ is independently —H, $C_1$-$C_{10}$ alkyl, —CN, —$CO_2R^7$, —$CONR^8R^9$, —$OR^{16}$, —$SR^{17}$, —$NR^{18}R^{19}$, —CO(AA)$_j$, —CONH(PS)$_k$, or X.

18. The method of claim 1 wherein each of $R^1$ to $R^3$ is independently —CN, —$CO_2R^7$, —$CONR^8R^9$, —$NR^{18}R^{19}$, or X.

19. The method of claim 1 wherein each of $R^1$ to $R^3$ is independently —CN, —$CONR^8R^9$, —$NR^{18}R^{19}$, or X.

20. The method of claim 1 wherein:
one of $R^1$, $R^2$, and $R^3$ is X; and
each of the other two of $R^1$, $R^2$, and $R^3$ is independently —CN, —$CONR^8R^9$, or —$NR^{18}R^{19}$.

21. The method of claim 1 wherein:
one of $R^1$, $R^2$, and $R^3$ is —CN, —$CONR^8R^9$, or —$NR^{18}R^{19}$; and
each of the other two of $R^1$, $R^2$, and $R^3$ is X.

22. The method of claim 1 wherein:

each of $R^1$ and $R^3$ is independently —H, —$OR^{16}$, —$SR^{17}$, or —$NR^{18}R^{19}$; and $R^2$ is —CN, —$CO_2R^7$, —$CONR^8R^9$, —$COR^{10}$, —$SO_2R^{12}$, —$CO(AA)_j$, —$CONH(PS)_k$, or X.

23. The method of claim 1 wherein each of $R^4$ to $R^{21}$ is independently —H, $C_1$-$C_{10}$ alkyl, —$(CH_2)_aOR^{23}$, —$CH_2(CHOH)_aR^{24}$, —$CH_2(CHOH)_aCO_2H$, —$(CHCO_2H)_aCO_2H$, —$(CH_2)_aNR^{25}R^{26}$, —$CH[(CH_2)_bNH_2]_aCO_2H$, —$CH[(CH_2)_bNH_2]_aCH_2OH$, —$CH_2(CHNH_2)_aCH_2NR^{27}R^{28}$, —$(CH_2CH_2O)_cR^{29}$, or —$(CH_2)_dCO(CH_2CH_2O)_cR^{30}$.

24. The method of claim 1 wherein each of $R^7$ to $R^{21}$ is independently —H, $C_1$-$C_{10}$ alkyl, or —$(CH_2)_aOR^{23}$.

25. The method of claim 1 wherein each of $R^7$ to $R^{21}$ is independently —H or $C_1$-$C_{10}$ alkyl.

26. The method of claim 1 wherein $(AA)_j$ is a polypeptide chain consisting of natural α-amino acids selected from aspartic acid, asparagine, arginine, histidine, lysine, glutamic acid, glutamine, serine, and homoserine.

27. The method of claim 26 wherein j is an integer from 1 to 20.

28. The method of claim 1 wherein $(PS)_k$ is a sulfated or non-sulfated polysaccharide chain consisting of glucose, fructose, mannose, and ribose.

29. The method of claim 28 wherein k is an integer from 1 to 20.

30. The method of claim 1 wherein each of a, b, and d is independently an integer from 1 to 6.

31. The method of claim 1 wherein c is an integer from 1 to 20.

32. The method of claim 1, wherein the pyrazine derivative is any of formula:

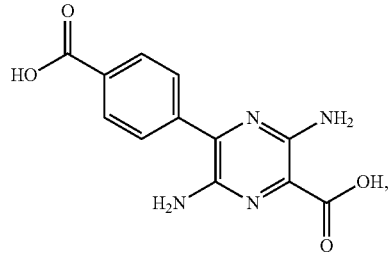

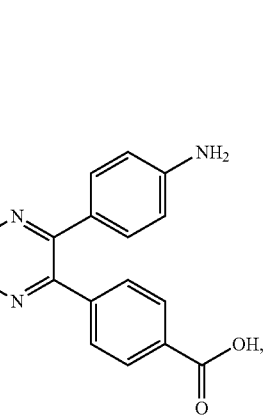

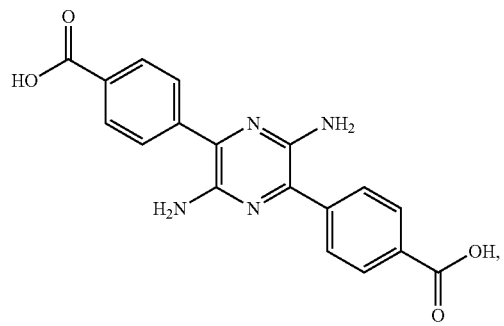

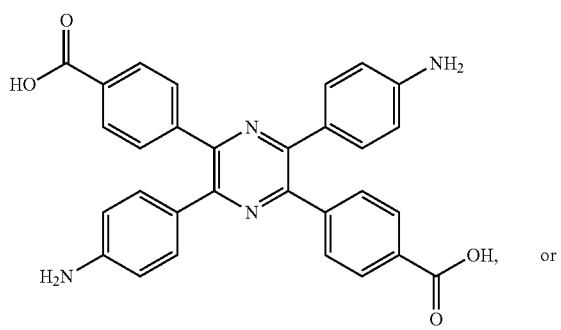

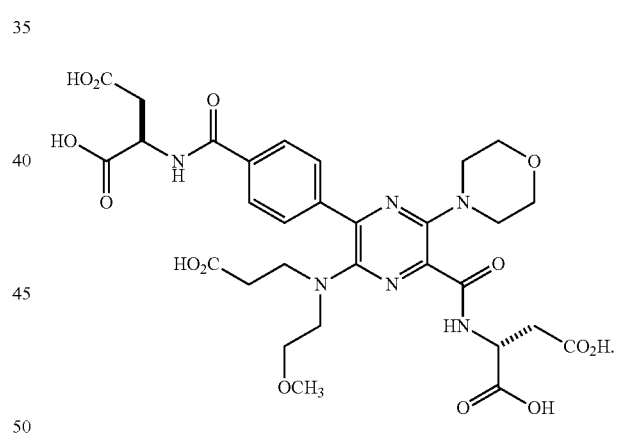

33. The method of claim 1, wherein the pyrazine derivative is any of formula:

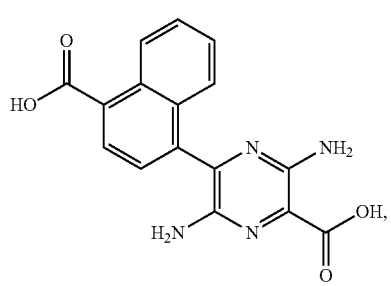

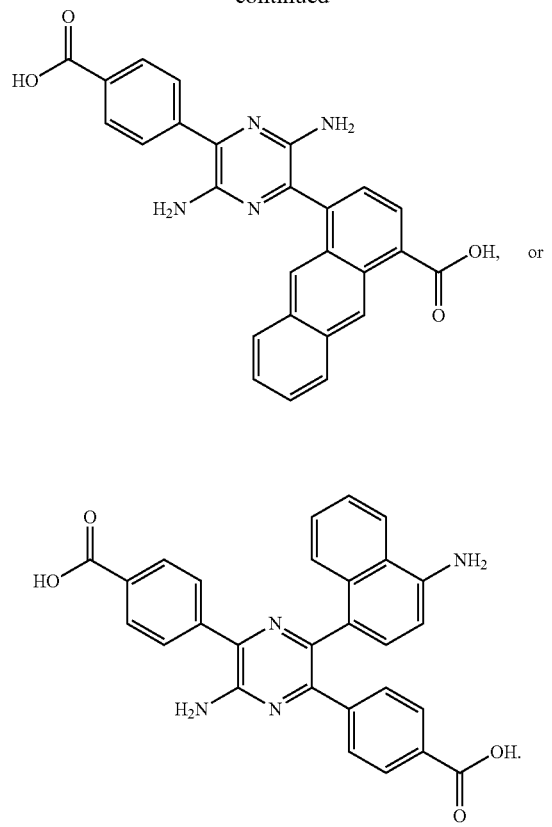
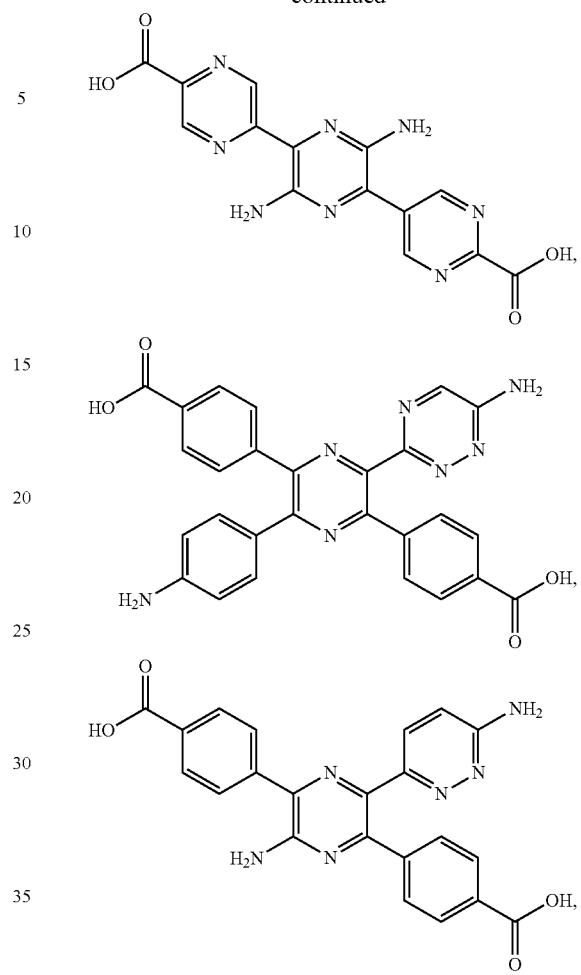
34. The method of claim 1, wherein the pyrazine derivative is any of formula:
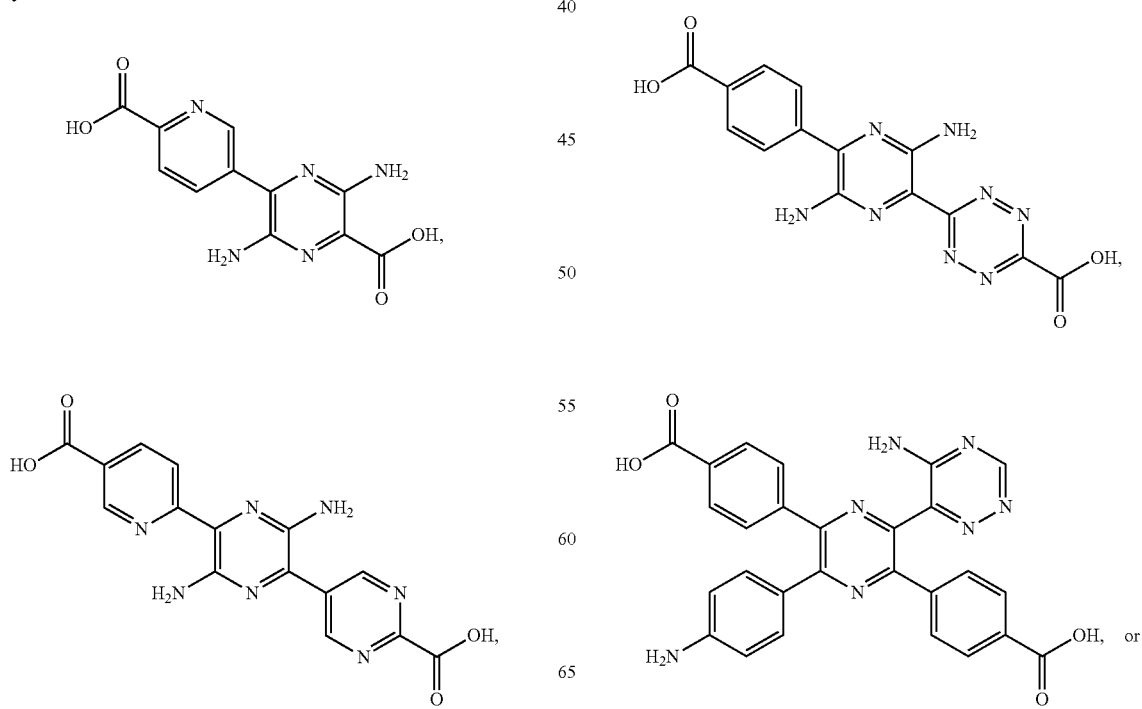

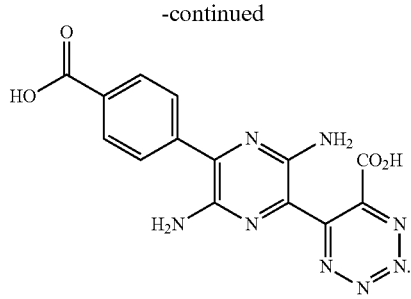
35. The method of claim 1, wherein the pyrazine derivative is any of formula:
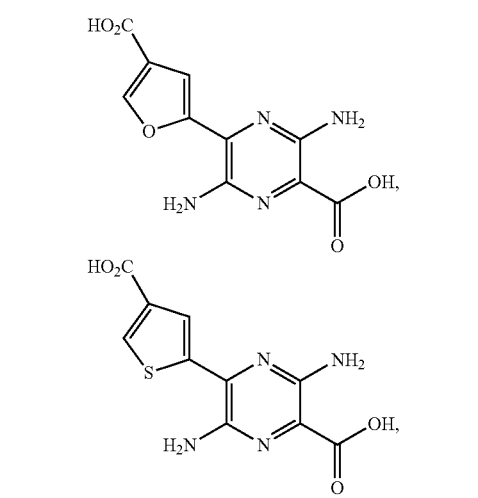
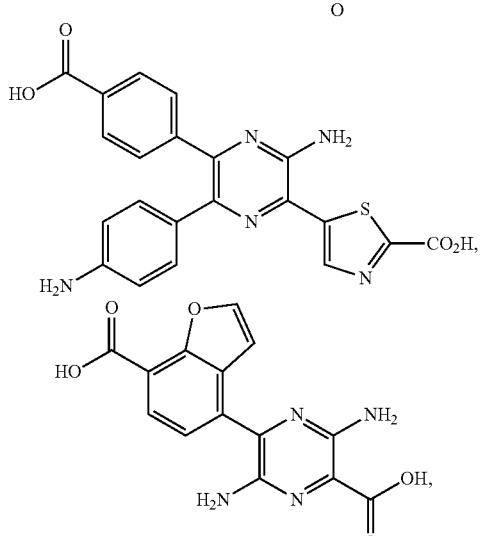
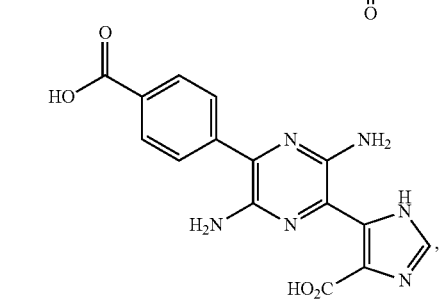
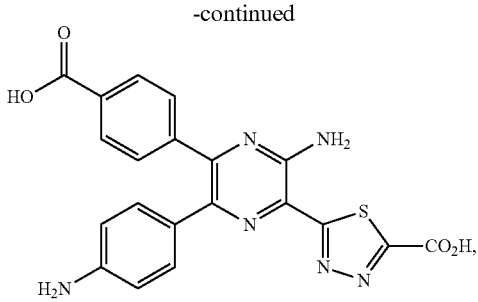
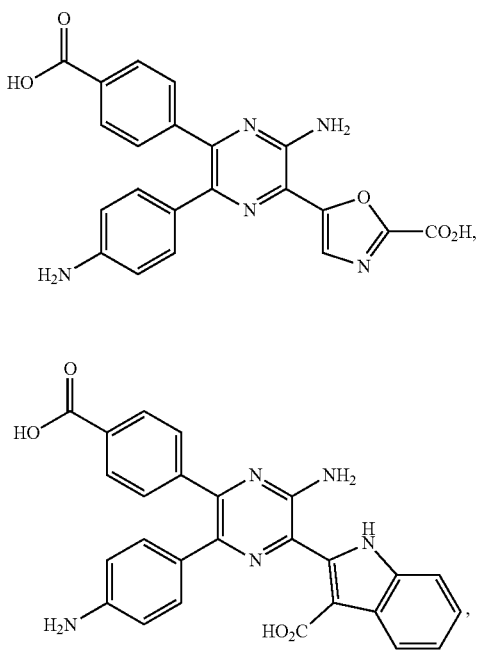
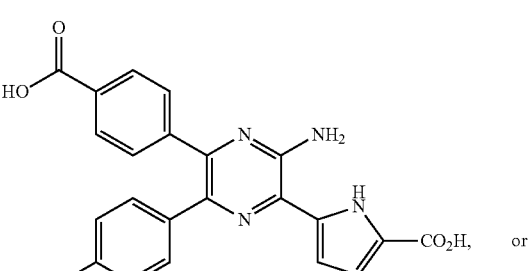
or
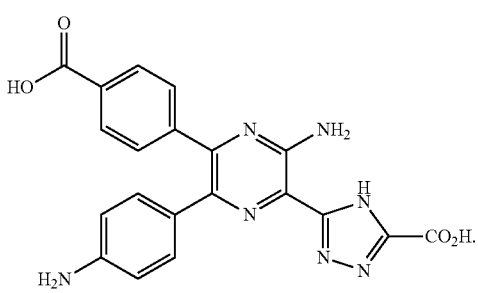

36. The method of claim 1, wherein the pyrazine derivative is any of formula:
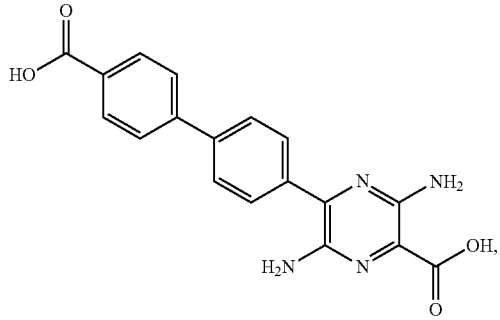
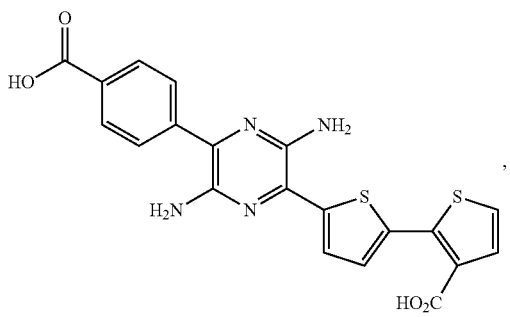
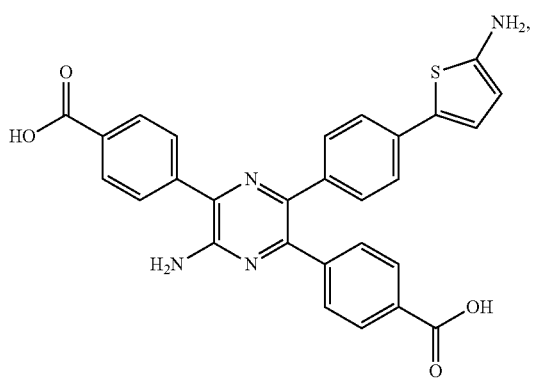
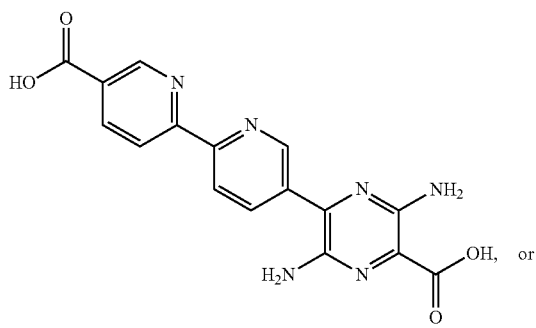
or
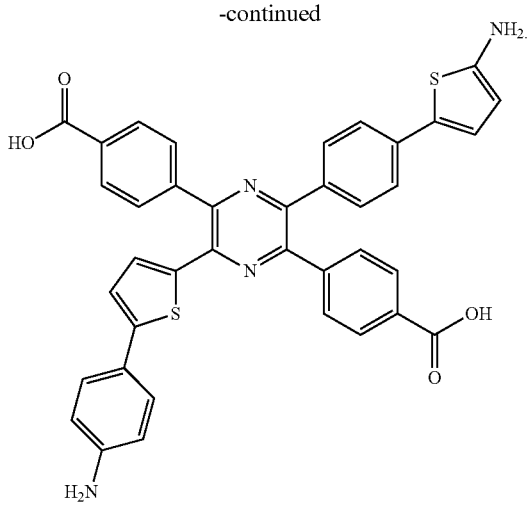
37. The method of claim 1, wherein the pyrazine derivative is any of formula:
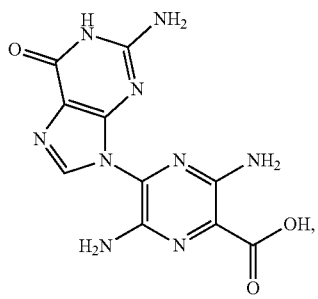
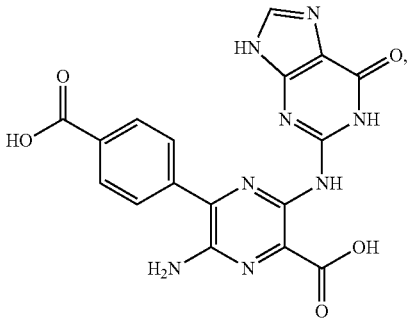
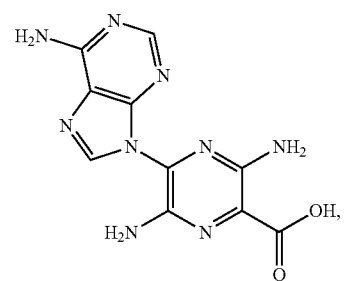

-continued
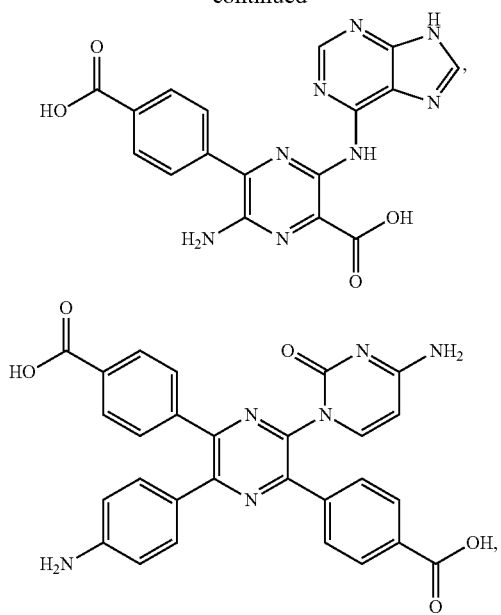
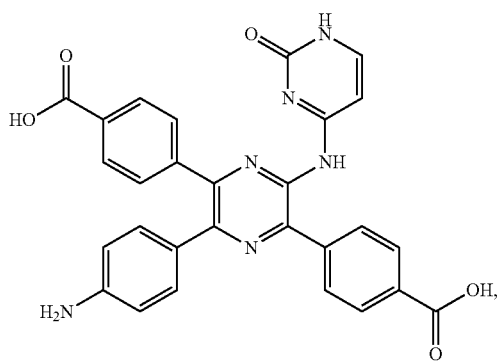
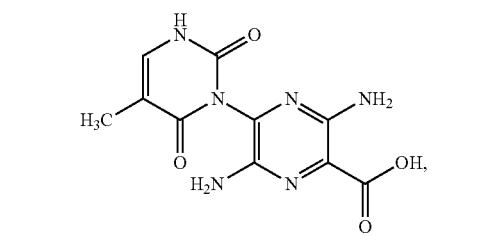
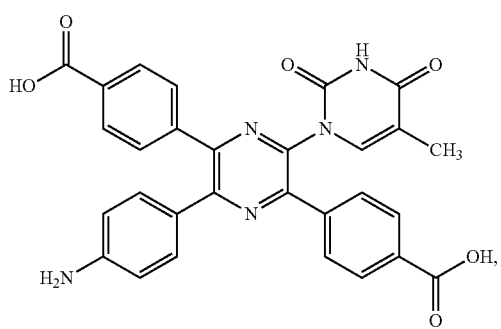
-continued
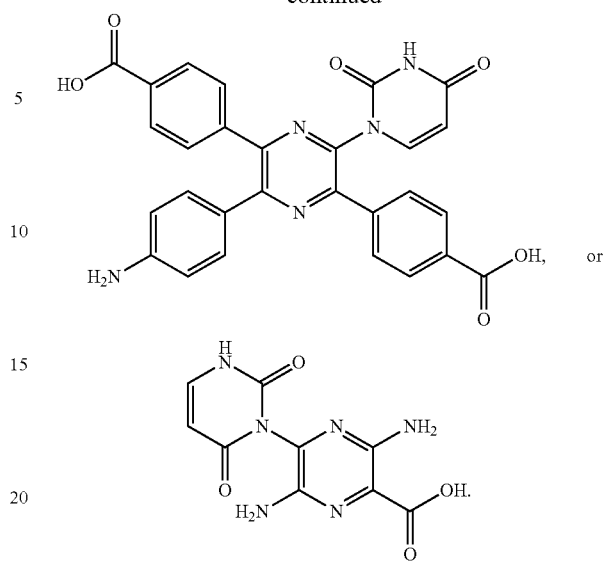
38. The method of claim 1, wherein the pyrazine derivative is any of formula:
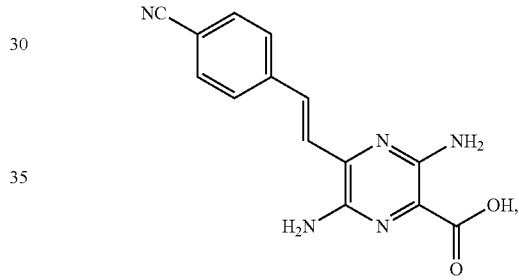
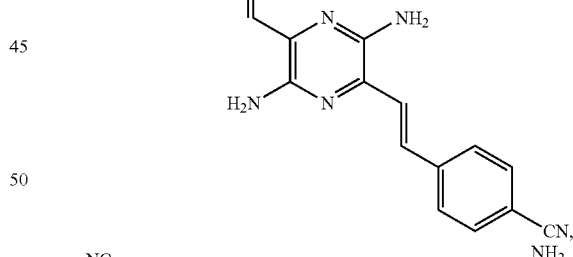
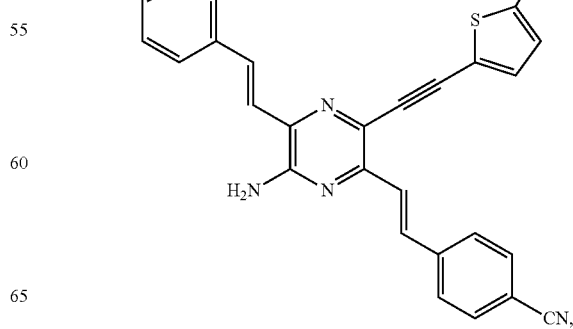

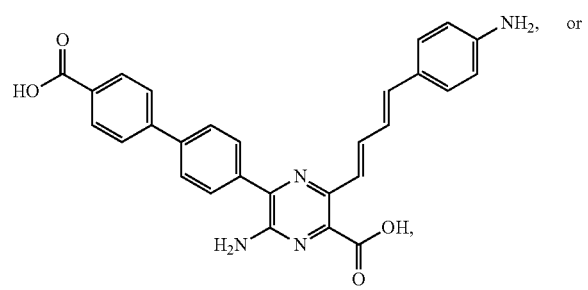
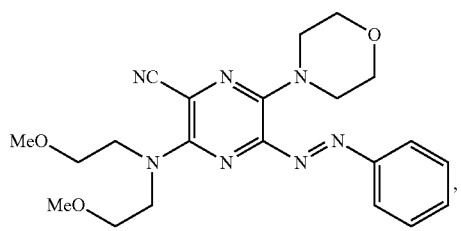
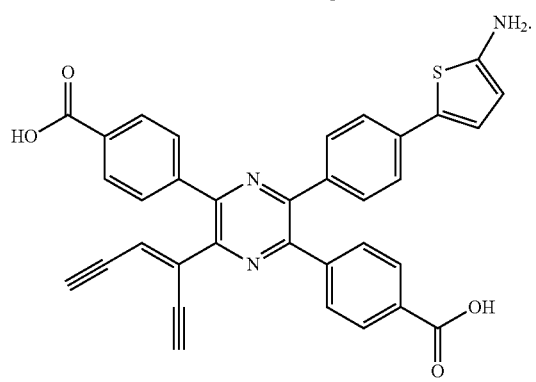
39. The method of claim 1, wherein the pyrazine derivative is any of formula:
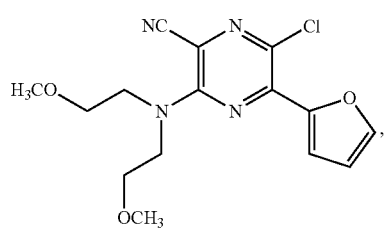
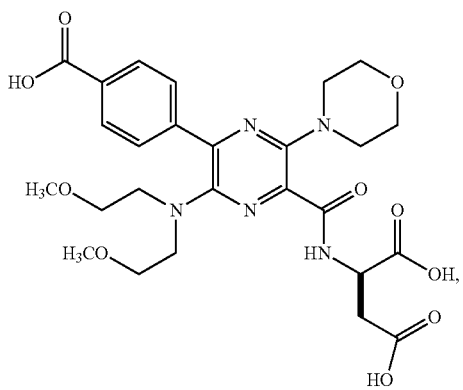
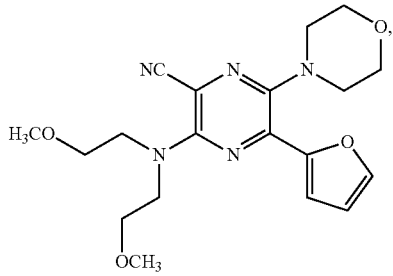
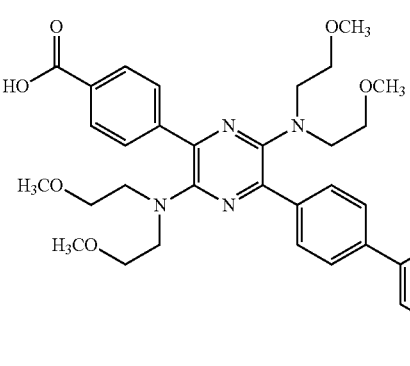
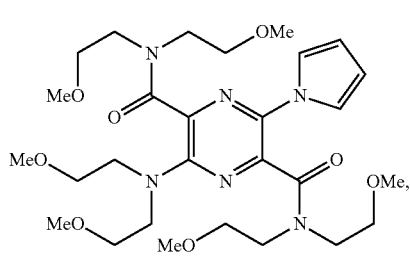
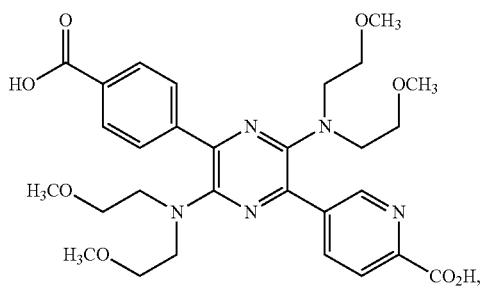

-continued
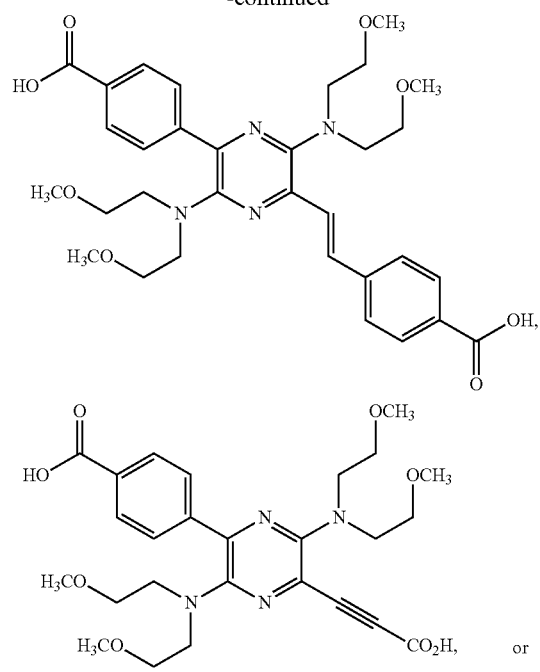
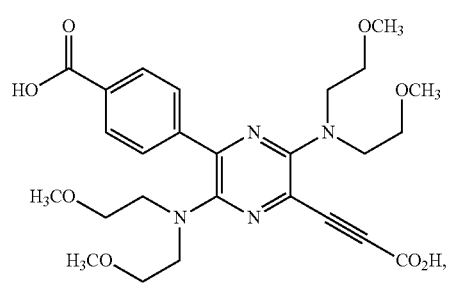
or
-continued
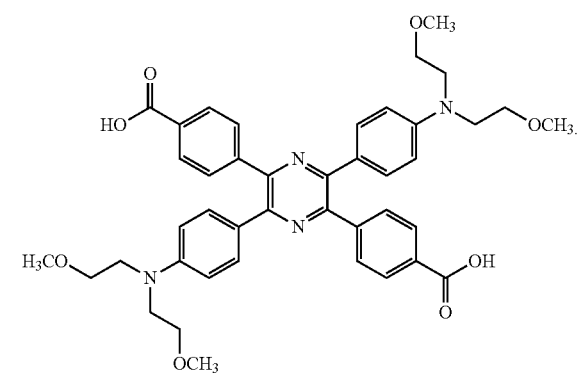 [SMILES: COCCN(CCOC)c1ccc(-c2nc(-c3ccc(C(=O)O)cc3)c(-c3ccc(N(CCOC)CCOC)cc3)nc2-c2ccc(C(=O)O)cc2)cc1]
* * * * *